US009394547B2

(12) United States Patent
Chen et al.

(10) Patent No.: US 9,394,547 B2
(45) Date of Patent: Jul. 19, 2016

(54) METHOD AND APPARATUS FOR DELIVERY OF MOLECULES TO CELLS

(71) Applicant: CITY UNIVERSITY OF HONG KONG, Hong Kong (CN)

(72) Inventors: Xianfeng Chen, Hong Kong (CN); Wenjun Zhang, Hong Kong (CN); Peng Shi, Shenzhen (CN)

(73) Assignee: CITY UNIVERSITY OF HONG KONG, Hong Kong (HK)

( * ) Notice: Subject to any disclaimer, the term of this patent is extended or adjusted under 35 U.S.C. 154(b) by 0 days.

(21) Appl. No.: 14/161,785

(22) Filed: Jan. 23, 2014

(65) Prior Publication Data

US 2014/0295558 A1    Oct. 2, 2014

Related U.S. Application Data

(63) Continuation-in-part of application No. 13/342,529, filed on Jan. 3, 2012, now abandoned.

(51) Int. Cl.
*B81B 1/00* (2006.01)
*A61M 37/00* (2006.01)
(Continued)

(52) U.S. Cl.
CPC ............... *C12N 15/89* (2013.01); *C12M 35/00* (2013.01)

(58) Field of Classification Search
CPC ............... B81B 1/00; A61M 37/0015; A61M 2037/003; A61M 2037/0046; C12M 35/00
See application file for complete search history.

(56) References Cited

U.S. PATENT DOCUMENTS 5,457,041 A    10/1995   Ginaven et al.
6,261,554 B1   7/2001    Valerio et al.
(Continued)

FOREIGN PATENT DOCUMENTS

EP        1195440 A1      4/2002
WO        2004035105 A2   4/2004
(Continued)

OTHER PUBLICATIONS

Han, et al., "Gene Expression Using an Ultrathin Needle Enabling Accurate Displacement and Low Invasiveness." Elsevier, Biochemical and Biophysical Research Communications 332 (2005) pp. 633-639.
(Continued)

*Primary Examiner* — Nathan Bowers
(74) *Attorney, Agent, or Firm* — Heslin Rothenberg Farley & Mesiti P.C.; Melvin S. Li, Esq.

(57) ABSTRACT

The present invention is concerned with a system and method for introducing a substance into cells. The system has an assembly including a plurality of elongate non-hollow nanoneedles forming a nanoneedle array or patch for delivering the substance into the cells, at least some of the nanoneedles have a non-uniform diameter with a wider upper end, a narrower lower end for penetration into the cells and a length from substantially 200 nm to 100 um. The lower end has a diameter from substantially 20-436 nm. Adjacent nanoneedles are spaced apart by substantially 5-50 um. The nanoneedles are made from a material selected from the group consisting of diamond, cubic boron nitride, carbon nitride, boron nitride, boron carbon nitride, metal borides and essentially boron materials, allowing the nanoneedles to maintain sufficient thinness and yet adequate rigidity during penetration. The nanoneedles are applied onto the cells grown on substrates at a preferred rate from 1 to 5 m/s. Alternatively, the nanoneedles are applied onto the cells grown on substrates by centrifugation force from 0.5 to 10 nN. Yet alternatively, the cells suspended in a fluid are applied to the nanoneedle array at a rate of 1 to 10 m/s.

4 Claims, 17 Drawing Sheets
(13 of 17 Drawing Sheet(s) Filed in Color)

(51) Int. Cl.
*C12M 1/00* (2006.01)
*C12N 15/89* (2006.01)
*C12M 1/42* (2006.01)

(56) References Cited

U.S. PATENT DOCUMENTS

| | | | | |
|---|---|---|---|---|
| 6,383,813 | B1* | 5/2002 | Baxter | C12M 35/00 435/285.1 |
| 6,620,617 | B2 | 9/2003 | Mathiowitz et al. | |
| 6,846,668 | B1* | 1/2005 | Garman | C12M 35/00 435/285.1 |
| 6,924,087 | B2 | 8/2005 | Yeshurun et al. | |
| 6,974,698 | B1* | 12/2005 | Miller | A61K 48/0008 435/375 |
| 7,112,442 | B2 | 9/2006 | Rice et al. | |
| 7,390,648 | B1* | 6/2008 | Palacios-Boyce | C12M 21/06 422/64 |
| 8,162,901 | B2 | 4/2012 | Gonnelli et al. | |
| 2004/0063100 | A1 | 4/2004 | Wang | |
| 2012/0171755 | A1 | 7/2012 | Peer et al. | |
| 2013/0005038 | A1 | 1/2013 | Nakamura | |

FOREIGN PATENT DOCUMENTS

| | | | |
|---|---|---|---|
| WO | 2010071918 | A1 | 7/2010 |
| WO | 2010082008 | A1 | 7/2010 |
| WO | 2011076537 | A1 | 6/2011 |

OTHER PUBLICATIONS

Yum, et al., "Mechanochemical Delivery and Dynamic Tracking of Fluorescent Quantum Dots in the Cytoplasm and Nucleus of Living Cells." Nano Letters, 2009, vol. 9, No. 5, pp. 2193-2198.

Zhang, et al., "Oriented Single-Crystal Diamond Cones and Their Arrays." Applied Physics Letter, 2003, vol. 82, No. 16, pp. 2622-2624.

Mehier-Humbert, et al., "Physical Methods for Gene Transfer: Improving the Kinetics of Gene Delivery Into Cells." Elsevier, Advanced Drug Delivery Reviews 57, 2005, pp. 733-753.

Yum, et al., "Nanoneedle: A Multifunctional Tool for Biological Studies in Living Cells," Nanoscale, first published as an Advance Article on the web Dec. 9, 2009.

Chen, et al., "A Cell Nanoinjector Based on Carbon Nanotubes," PNAS, 2007, vol. 104, No. 20, pp. 8218-8222.

Zhang, et al., "Structuring Nanodiamond Cone Arrays for Improved Field Emission." Applied Physics Letters, 2003, vol. 83, No. 16, pp. 3365-3367.

Kim, et al., "Interfacing Silicon Nanowires with Mammalian Cells." JACS, 2007, vol. 129, No. 23, pp. 7228-7229.

Shalek, et al., "Vertical Silicon Nanowires as a Universal Platform for Delivery Biomoleculres into Living Cells," PNAS, 2010, vol. 107, No. 5, pp. 1870-1875.

Foerg, et al., "On the Biomedical Promise of Cell Penetrating Peptides: Limits Versus Prospects." Journal of Pharmaceutical Sciences, 2008, vol. 97, No. 1, pp. 144-162.

Rubinsky, "Irreversible Electroporation in Medicine." Technology in Cancer Research and Treatment, 2007, vol. 6, No. 4, pp. 255-259.

Savulescu, "Harm, Ethics Committees and the Gene Therapy Death." Journal of Medical Ethics, 2001, vol. 27, pp. 148.150.

Chaudhri, et al., "Out-of-Plane, High Strength, Polymer Microneedles for Transdermal Drug Delivery." 33rd Annual International Conference of the IEEE EMBS, 2001, pp. 3680-3683.

Chu, et al., "Fabrical of Dissolving Polymer Microneedles for Controlled Drug Encapsulation and Delivery: Bubble and Pedestal Microneedle Designs." Journal of Pharmaceutical Sciences, vol. 99, No. 10, pp. 4228-4238.

Kim, et al., "Efficient and Facile Delivery of Gold Nanoparticles in vivo Using Dissolvable Microneedles for Contrast-Enhanced Optical Coherence Tomography." Biomedical Optics Express, 2010, vol. 1, No. 1, pp. 106-113.

Lee, et al., "Dissolving Microneedles for Transdermal Drug Delivery." Biomaterials, 2008, vol. 29, pp. 2113-2124.

Park, et al., "Biodegradable Polymer Microneedles; Fabrication, Mechanics, and Transdermal Drug Delivery." Elsevier, Journal of Controlled Release, 2005, vol. 104, pp. 51-66.

Martin, et al., "Low Temperature Fabrication of Biodegradable Sugar Glass Microneedles for Transdermal Drug Delivery Applications." Journal of Controlled Release, 2012, vol. 158, pp. 93-101.

Park, et al, "Analysis of Mechanical Failure of Polymer Microneedles by Axial Force." Journal of Korean Physics Soc., 2010, vol. 56, No. 4, pp. 1223-1227.

Raphael, et al., "Targeted, Needle-Free Vaccinations in Skin Using Multilayered, Densely-Packed Dissolving Microprojection Arrays." Small, 2010, vol. 6, No. 16, pp. 1785-1793.

Sullivan, et al., "Minimally Invasive Protein Delivery with Rapidly Dissolving Polymer Microneedles," Adv. Mater, 2008, vol. 20, pp. 933-938.

Sullivan, et al., "Dissolving Polymer Microneedle Patches for Influenza Vaccination." Nature Medicine, 2010, pp. 1-7.

Wang, et al., "Recent Advances in the Synthesis and Application of Layered Double Hydroxide (LDH) Nanosheets." American Chemical Society, 2012, vol. 112, pp. 4124-4155.

* cited by examiner

METHOD AND APPARATUS FOR DELIVERY OF MOLECULES TO CELLS

CROSS REFERENCE TO RELATED APPLICATION

The present application is a continuation-in-part application of U.S. patent application Ser. No. 13/342,529 filed on Mar. 1, 2012, contents of which are incorporated herein in its entirety.

FIELD OF THE INVENTION

The present invention is concerned with a system and method for delivery of molecules, e.g. drug, gene, to cells.

BACKGROUND OF THE INVENTION

Cell therapy has become very attractive in medical technology in recent years because it provides a unique opportunity to treat certain diseases (e.g. human liver cirrhosis). In cell therapies, molecules, drugs or genes such as plasmid DNA, sRNA, miRNA, shRNA, nanoparticle or nanowire are to be delivered to the cell cytoplasm or nuclei in order that they become functional and therapeutic. Such molecules play important roles in medical treatment. However, these molecules are typically rather complicated and cannot penetrate cell membranes efficiently or effectively by simple diffusion. Various approaches have been suggested to deliver these molecules to cells such as cell penetrating peptides, electroporation, ballistic nanoparticle delivery, viral vectors and nanoneedles. However, they suffer from different limitations. One of the challenges is that the cells are very delicate and fragile. Thus, when attempting to penetrate their cell membrane they often sustain excessive cell damage causing cell death. Other challenges include whether means for use in introducing the molecules to the cells are effectively structured to ensure successful or effective delivery. As such, a vast number of different factors are to be taken into consideration in achieving a balance of successful delivery.

The present invention seeks to address some of the problems in delivering molecules into a subject and in particular within cells or nucleus of the cells, or at least to provide an alternative to the public.

SUMMARY OF THE INVENTION

According to a first aspect of the present invention, there is provided a system for introducing a substance into cells, comprising an assembly including a plurality of elongate non-hollow nanoneedles forming a nanoneedle patch for delivering the substance into the cells, at least some of the nanoneedles have a non-uniform diameter with a wider upper end, a narrower lower end for penetration into the cells and a length from substantially 200 nm to 100 um, wherein the lower end has a diameter from substantially 20-436 nm, wherein adjacent nanoneedles are spaced apart by substantially 5-50 um, wherein a) the nanoneedles are made from a material selected from the group consisting of diamond, cubic boron nitride, carbon nitride, boron nitride, boron carbon nitride, metal borides and essentially boron materials, allowing said nanoneedles to maintain sufficient thinness and yet adequate rigidity during penetration, and applying the cells suspended in a fluid to the nanoneedle array at a rate from 1 to 10 m/s, alternatively, applying the nanoneedles onto the cells grown on substrates by centrifugation force from 0.5 to 10 nN, and yet alternatively applying the nanoneedles onto the cells grown on substrates at a speed of 0-5 m/s. The substance to be delivered to cells can be coated on the lower end of the nanoneedles or dissolved in the cell suspension or dissolved in a medium sounding the cells.

Preferably, the nanoneedle patch may have a nanoneedle density of $10^5$-$10^6$ nanoneedles per $cm^2$.

In an embodiment, the upper end may have a diameter from 50 nm-20 um.

In one embodiment, the substance may be a bio-agent or selected from a group including drug molecules, gene molecules such as plasmid DNA, sRNA, miRNA, shRNA, nanoparticles and nanowires.

The system may comprise a substrate supporting the cells. The substrate may be a multi-well array of container.

The system may be configured to adopt a generally conical or cylindrical profile.

The system may comprise means for applying the micro-nanoneedle patch to the cells at a speed of 0-5 m/s. In a specific embodiment, the speed may be 0-3 m/s.

According to a second aspect of the present invention, there is provided a method of delivering substance to target cells, comprising steps of providing a system as described above, and the substance to be delivered be released from the nanoneedles intra-cellularly, or substance be diffused into the cells. Preferably, the method may include a further step of applying nanoneedle patch to the cells under centrifugation at a speed from 300-1000 rpm (12.8-142 g, RCF).

BRIEF DESCRIPTION OF DRAWING(S)

Different embodiments of the present invention are now described, by way of example only, with reference to the following drawing in which:—

This patent or application file contains at least one drawing executed in color. Copies of this patent or patent application publication with color drawing(s) will be provided by the Office upon request and payment of the necessary fee.

Figure 4:
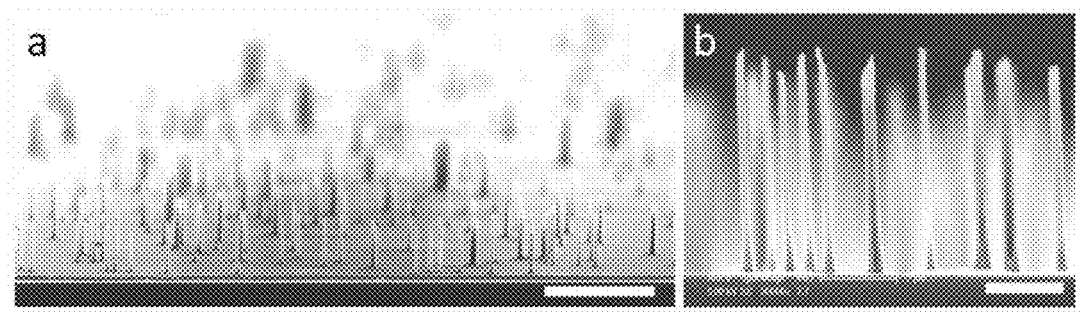
Figure 5:
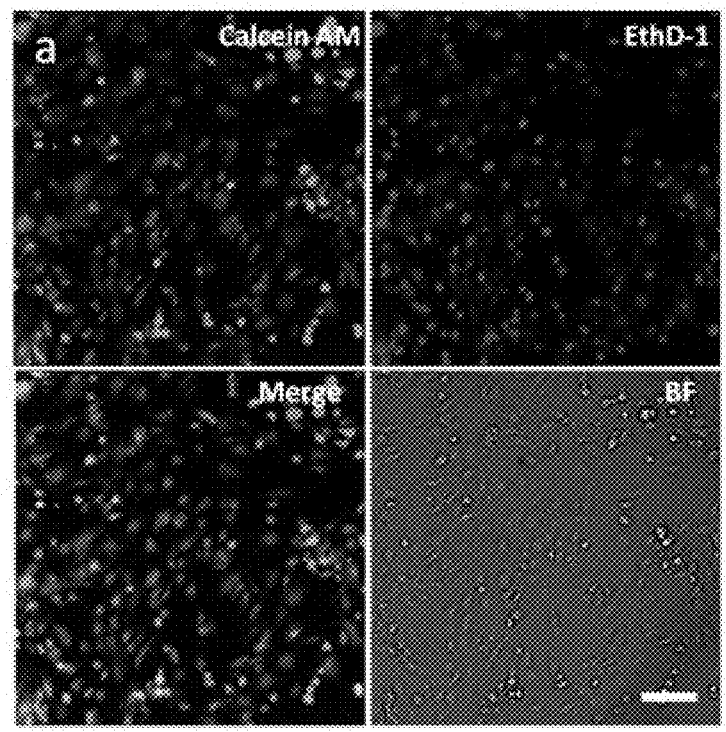
Figure 5B:
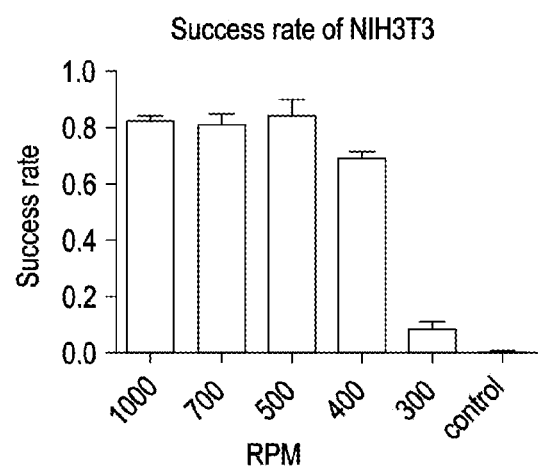
Figure 5C:
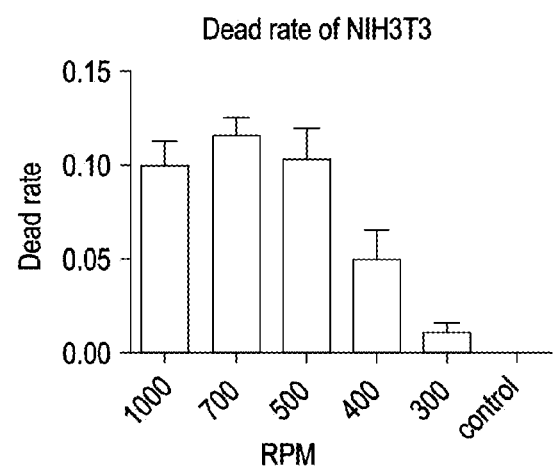
Figure 6:
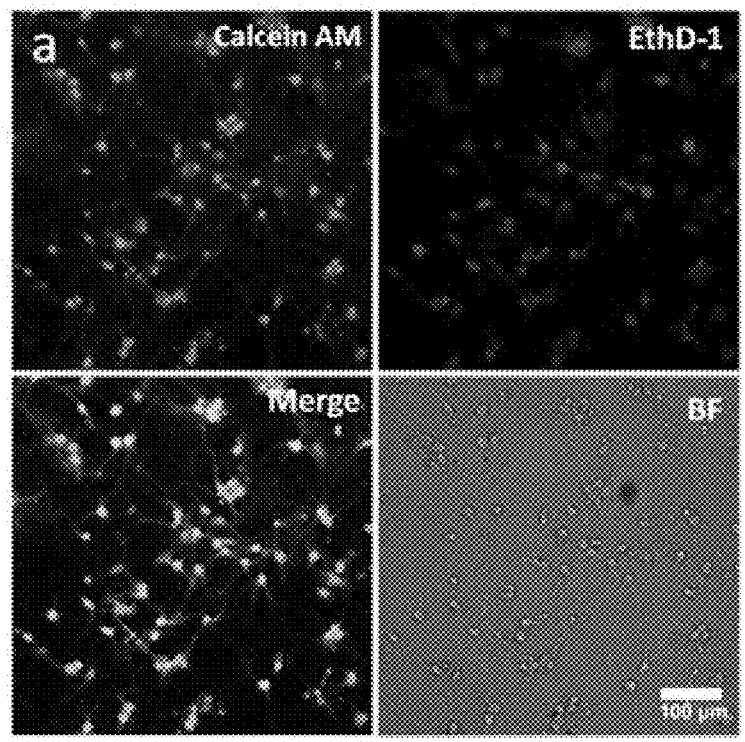
Figure 6B:
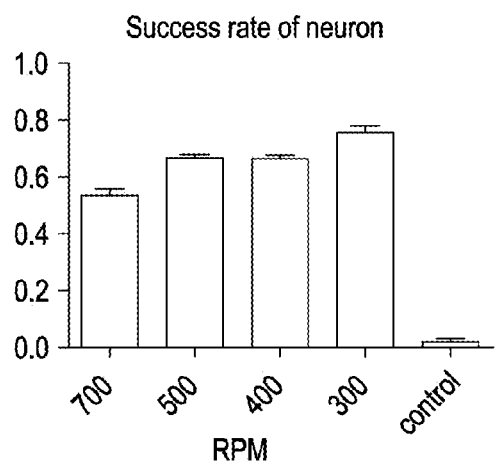
Figure 6C:
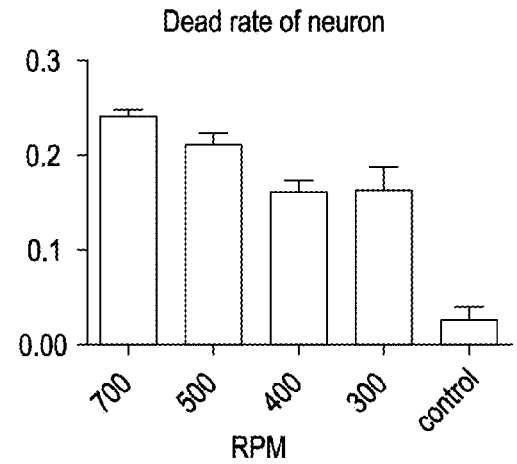
Figure 7:
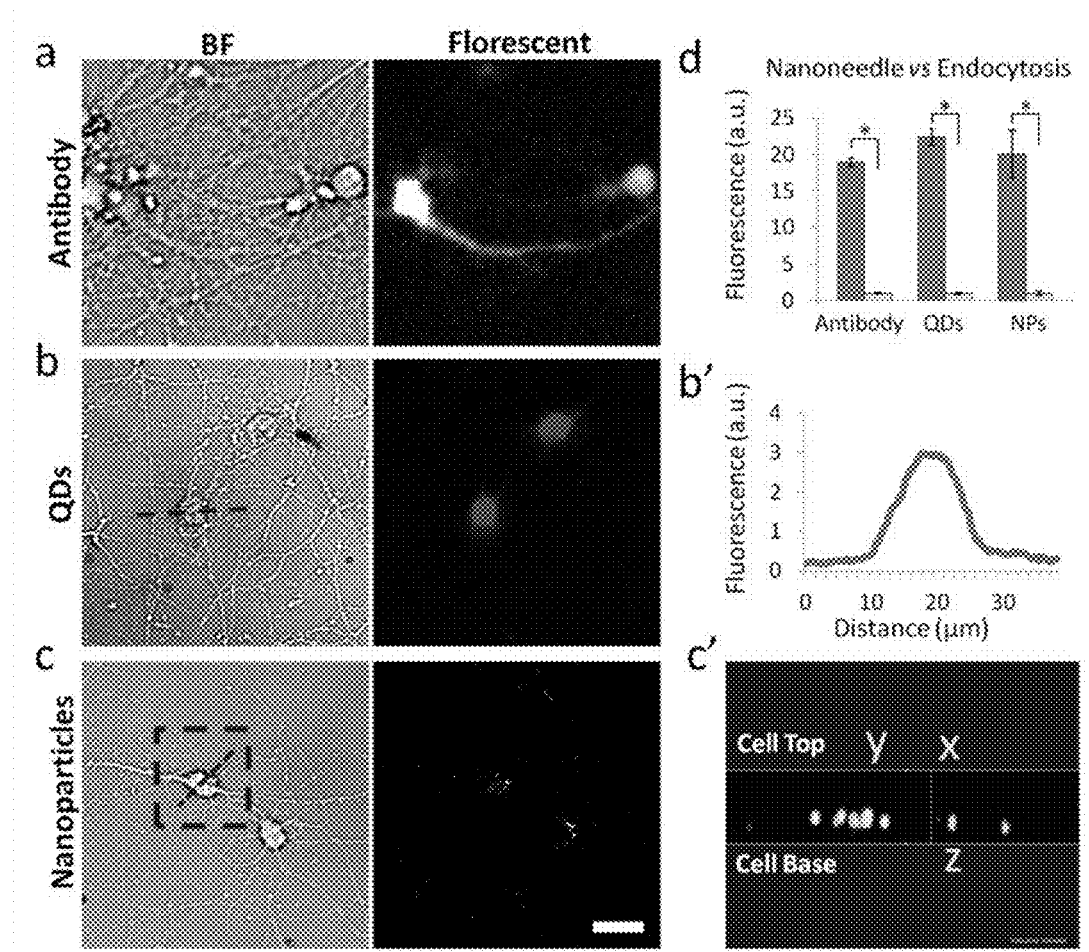
Figure 8:
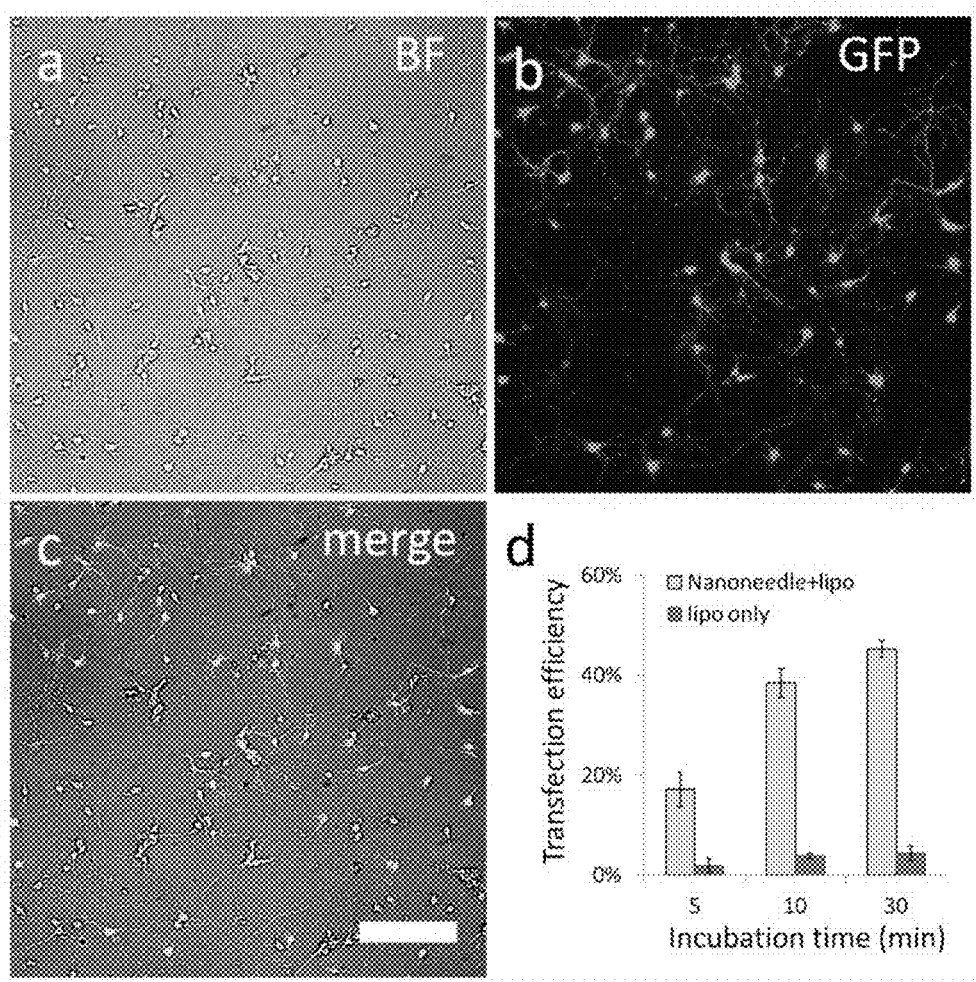
Figure 9:
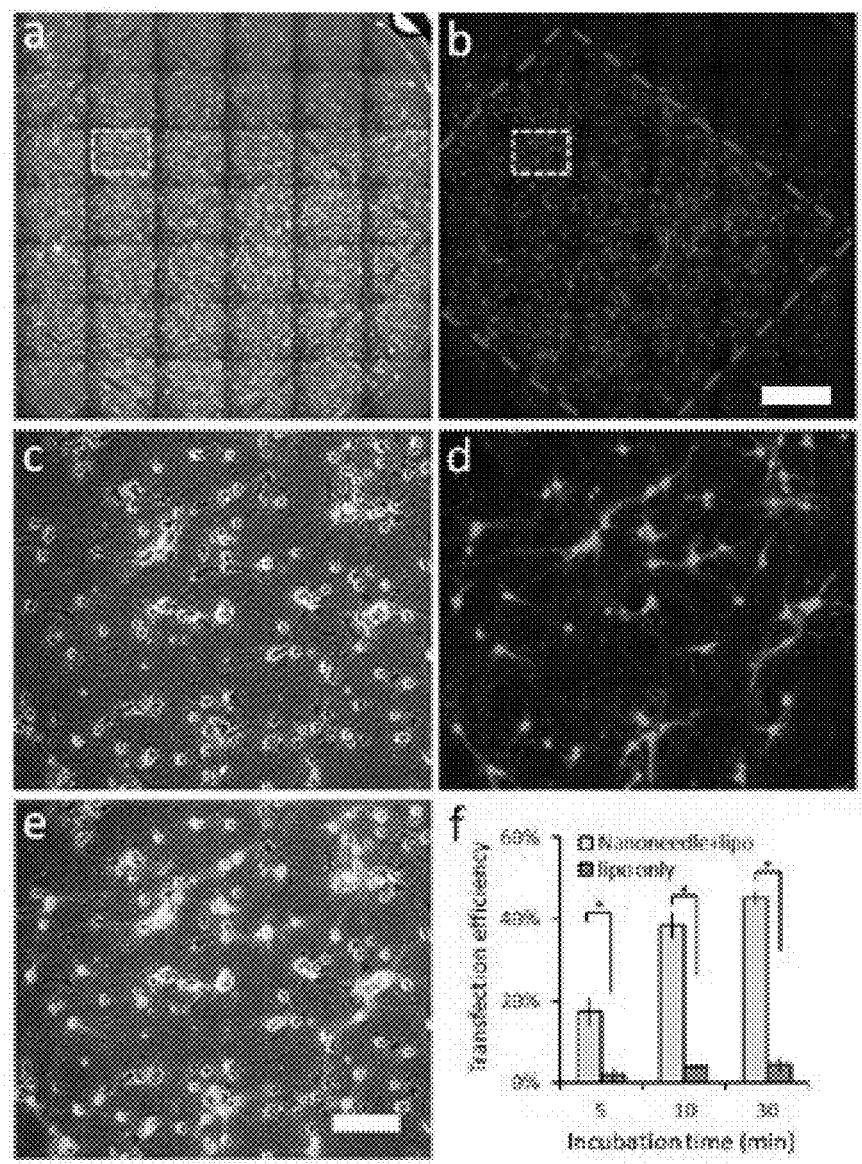
Figure 10:
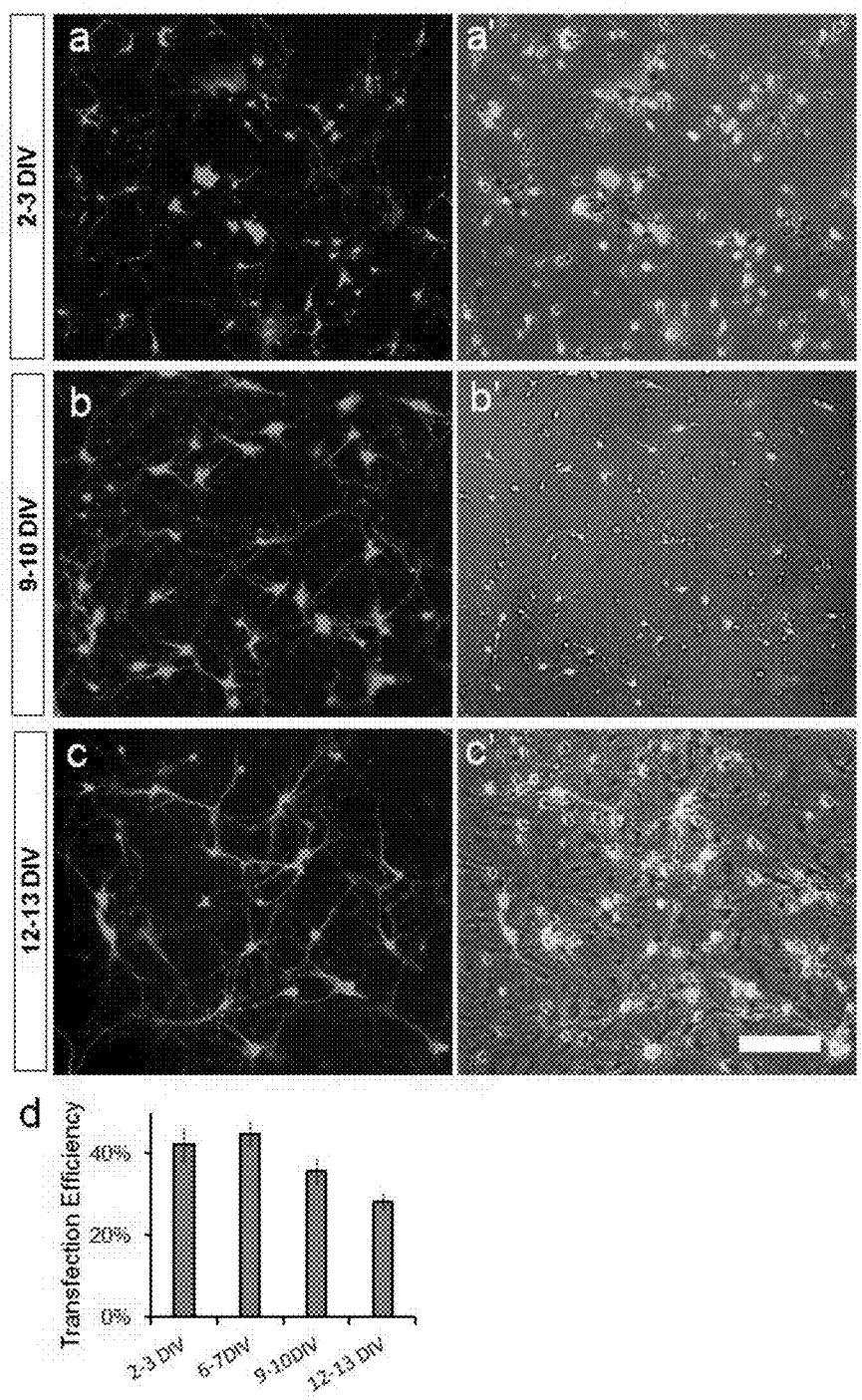

FIG. 3a) is a schematic diagram showing a nanoneedle array based intracellular delivery system according to the present invention;

FIG. 3b illustrates an experiment showing the work flow of substance delivery procedures using nanoneedle patches; in particular, penetration and subsequent disruption of cell membrane by nanoneedles was precisely-controlled by centrifugation-induced supergravity to achieve reliable, highly efficient, diffusion based cytosolic delivery;

FIGS. 4a and 4b are photographic representations of a nanoneedle patch of the embodiment shown in FIG. 4;

FIGS. 5a, 5b, and 5c included in FIG. 5, Drawings Sheet 3/17, are photographic representations and charts showing effects of centrifugation speed on delivery efficiency in fibroblast cells;

FIGS. 6a, 6b, and 6c included in FIG. 6, Drawings Sheet 4/17, are photographic representations and charts showing effects of centrifugation speed on delivery efficiency in primary neuron cells;

FIG. 7 are photographic representations and charts showing delivery of various molecules and materials into neurons (FIG. 7a: Bright field and florescent images of neurons loaded with antibodies, donkey IgG labeled with alexa fluor 647; FIG. 7b: Bright field and fluorescent images of neurons loaded with QDs, 625 nm emission wavelength; FIG. 7b': Distribution of QD fluorescence signal in a neuron; FIG. 7c: Bright field and florescent images of neurons loaded with 200 nm polystyrene nanoparticles, scale bar, 20 μm; FIG. 7c': A cross-section image of a 3d reconstructed cell from Z-series fluorescent images of the boxed cell in panel (c); FIG. 7d: Comparison of the delivery efficiencies of the nanoneedle array based technique and endocytosis based internalization of different materials, n>20 for each condition, *p<0.01 by Kruskal-Wallis test);

FIGS. 8a, 8b, 8c, and 8d included in FIG. 8, Drawings Sheet 6/17, are photographic representations and a chart showing ultrafast and highly efficient cytosolic delivery of plasmid DNAs in neurons;

FIG. 9 are photographic images and a graph showing ultrafast and highly efficient cytosolic delivery of plasmid DNAs in neurons achieved by using system according to the present invention; and FIGS. 10a, 10a', 10b, 10b', 10c, 10c', and 10d included in FIG. 10, Drawings 8/17, are photographic images and a graph showing delivery of DNA plasmid in cultured primary neurons of different stages.

Figure 11:
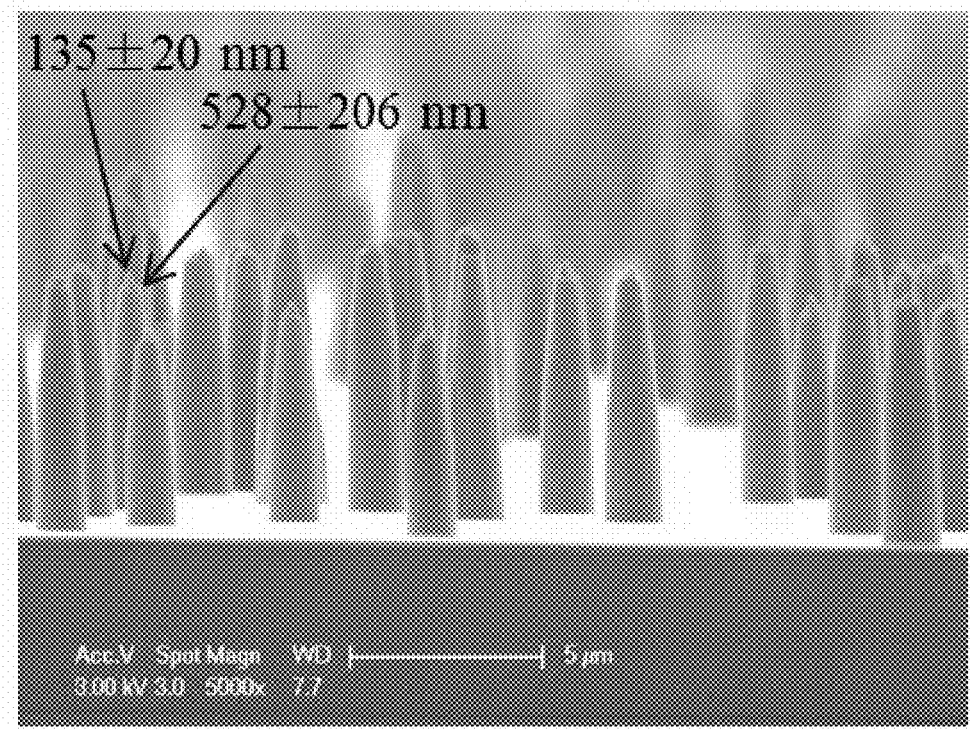
Figure 12:
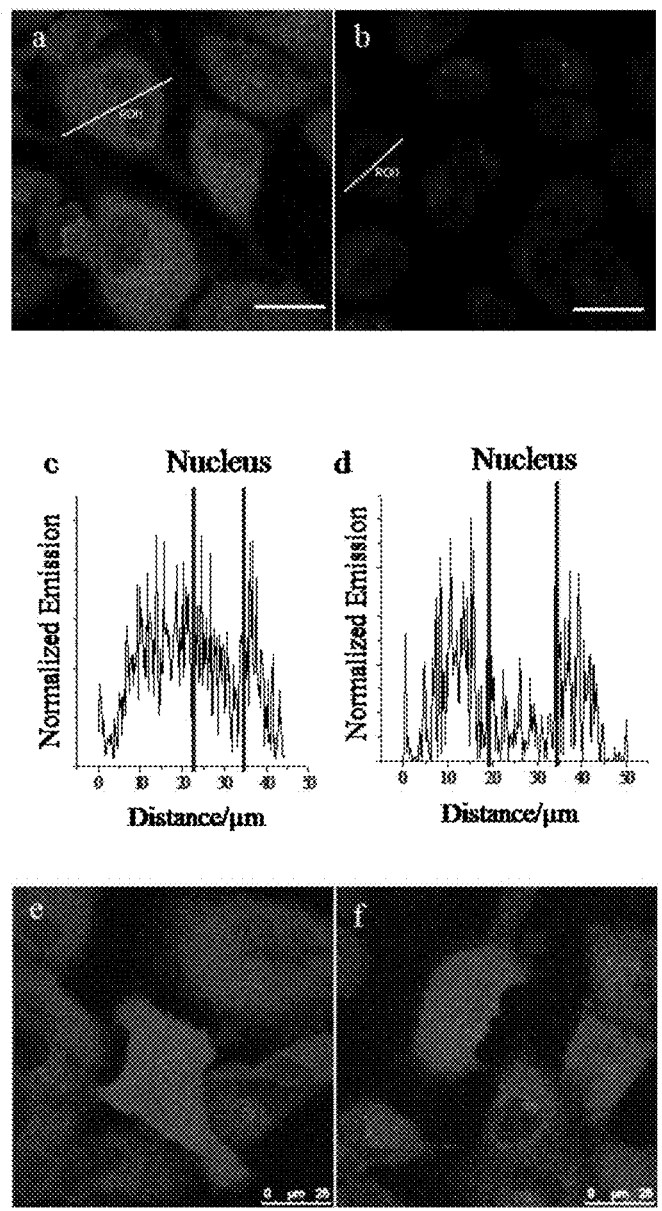
Figure 13:
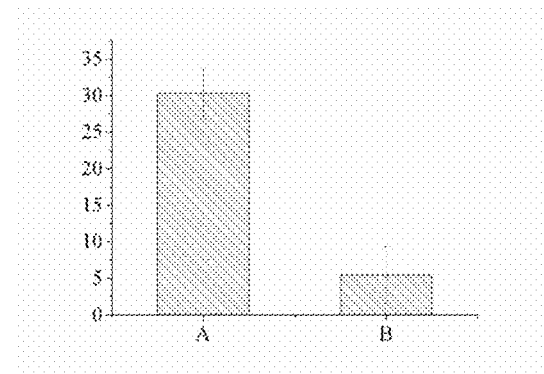
Figure 14:
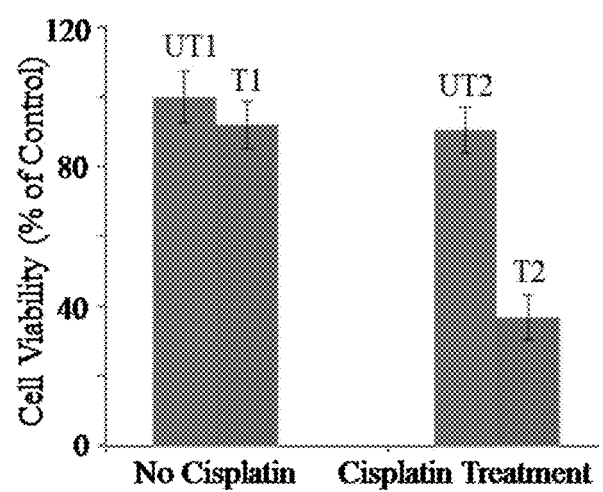
Figure 15:
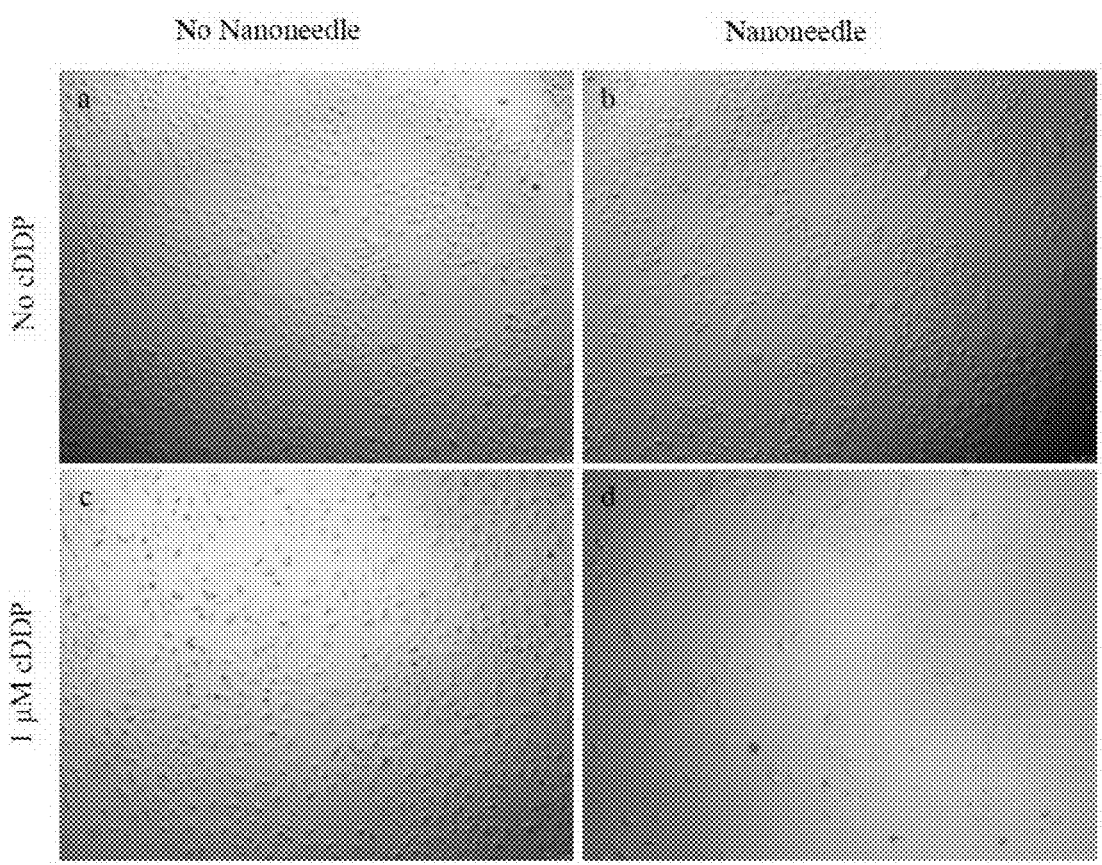

FIG. 11 is a SEM image of an array of diamond needles in accordance with another embodiment of the present invention;

FIGS. 12a and 12b are confocal images of diamond nanoneedles treated cells and untreated cells, respectively, after 19 hours incubation with luminescent iridium (III) polypyridine complex;

FIGS. 12c and 12d are charts showing normalized emission intensity over the lines drawn crossing over cells in FIGS. 13a and 13b, respectively;

FIGS. 12e and 12f are confocal microscopy images of diamond nanoneedles treated cells after 19 hours incubation with luminescent iridium (III) polypyridine complex;

FIG. 13 is a chart illustrating a fluorescence intensity analysis in the nuclei of the cells with (A) and without (B) diamond nanoneedle array treatment;

FIG. 14 is a chart showing viability of cells (of FIG. 15) at 72 hours post plating;

FIG. 15 are photographic representations of bright field images of cells at 72 hours after plating; cells shown in FIGS. 15a-d were treated under different conditions;

—and—

Figure 16:
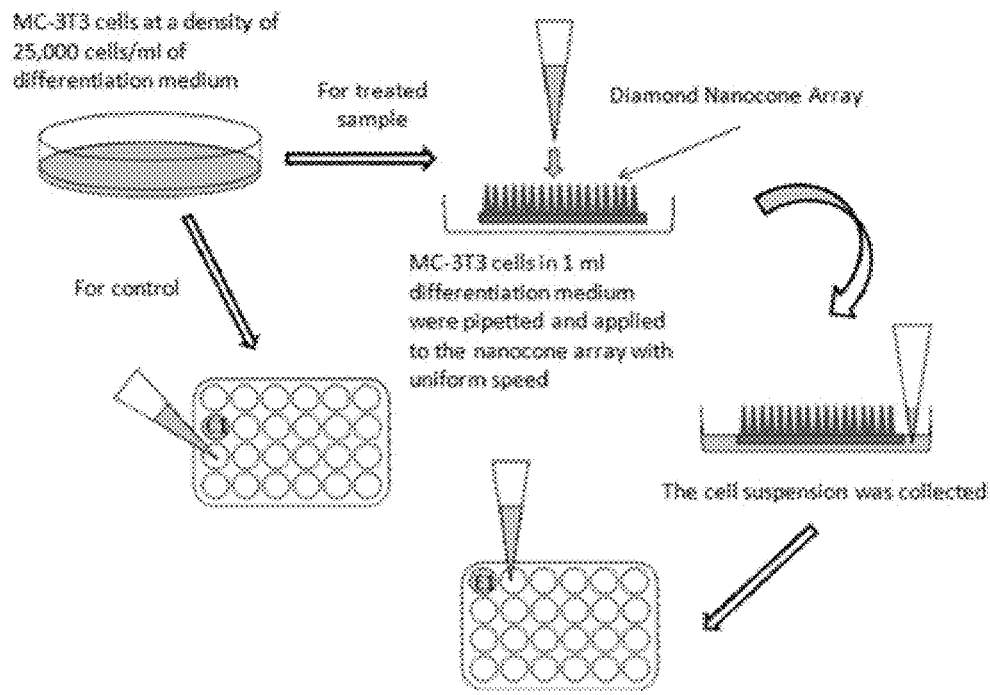
Figure 17:
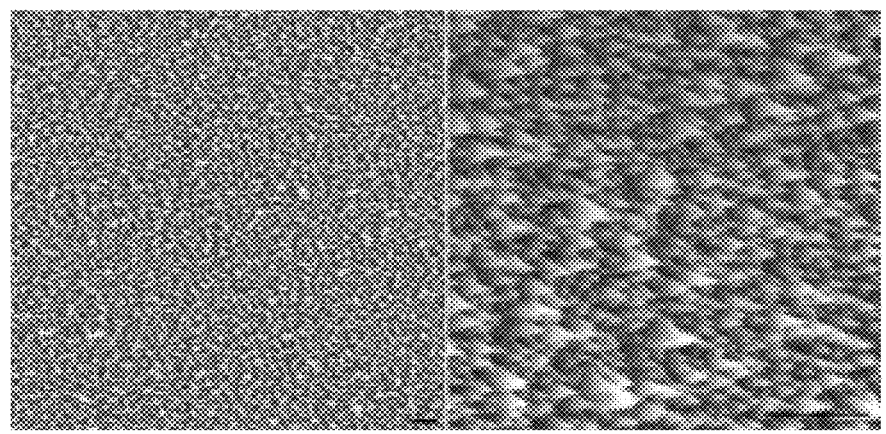
Figure 19:
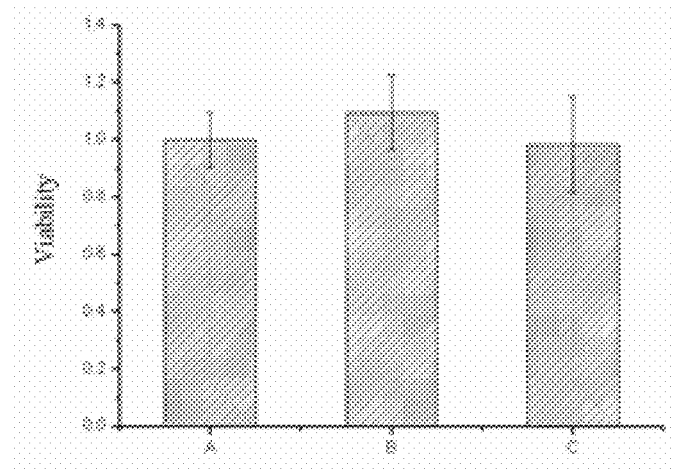
Figure 20:
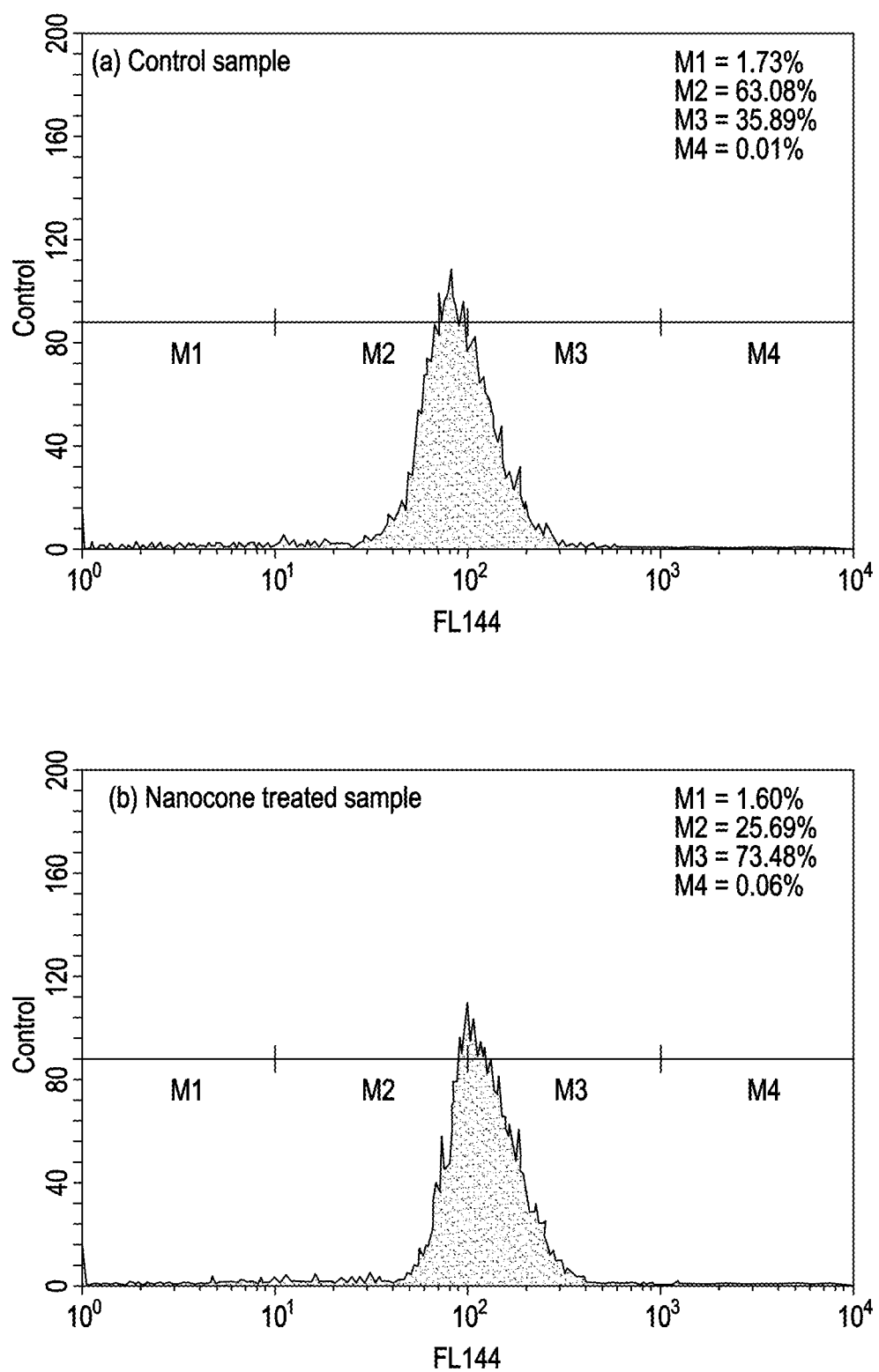
Figure 21:
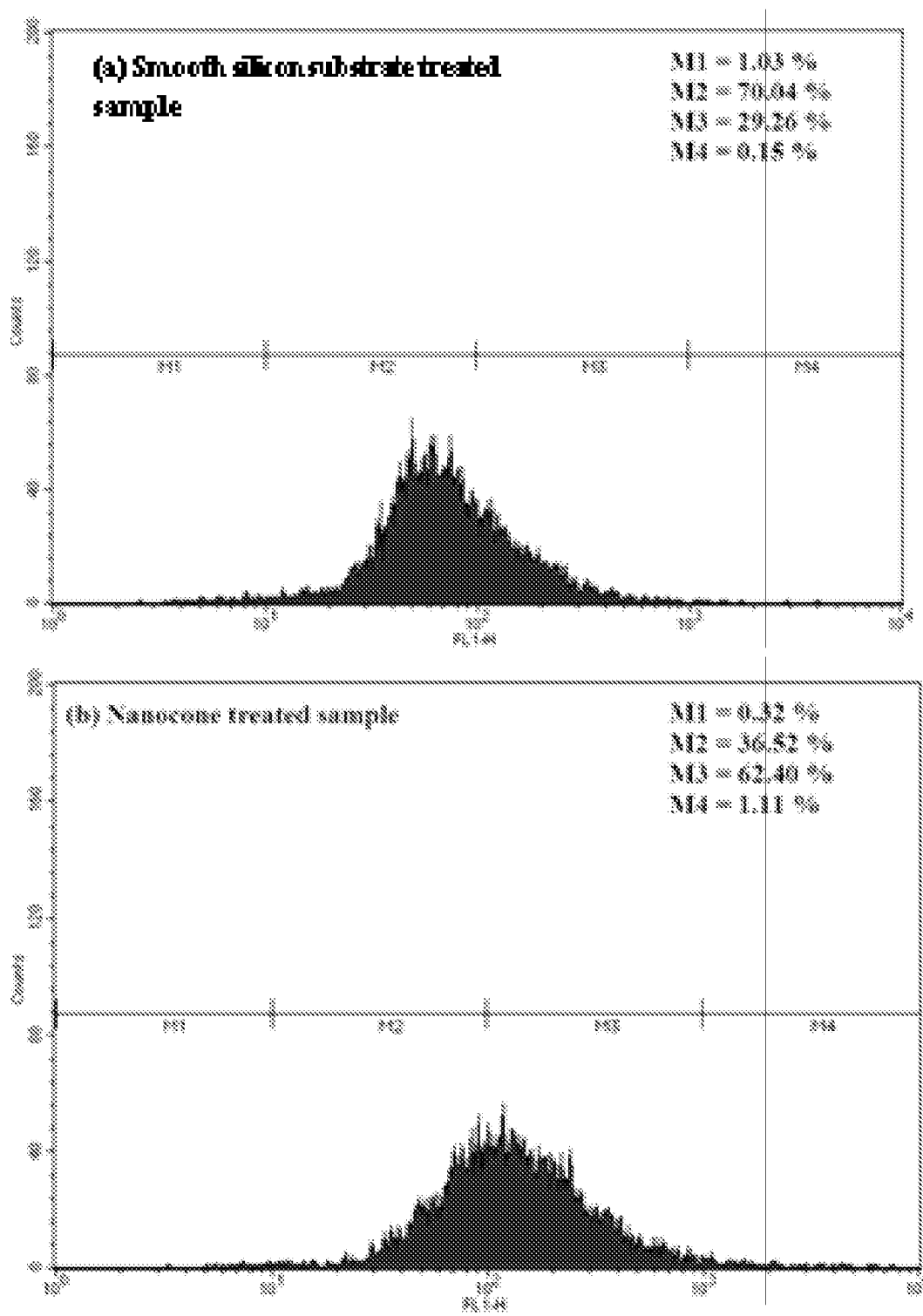
Figure 22:
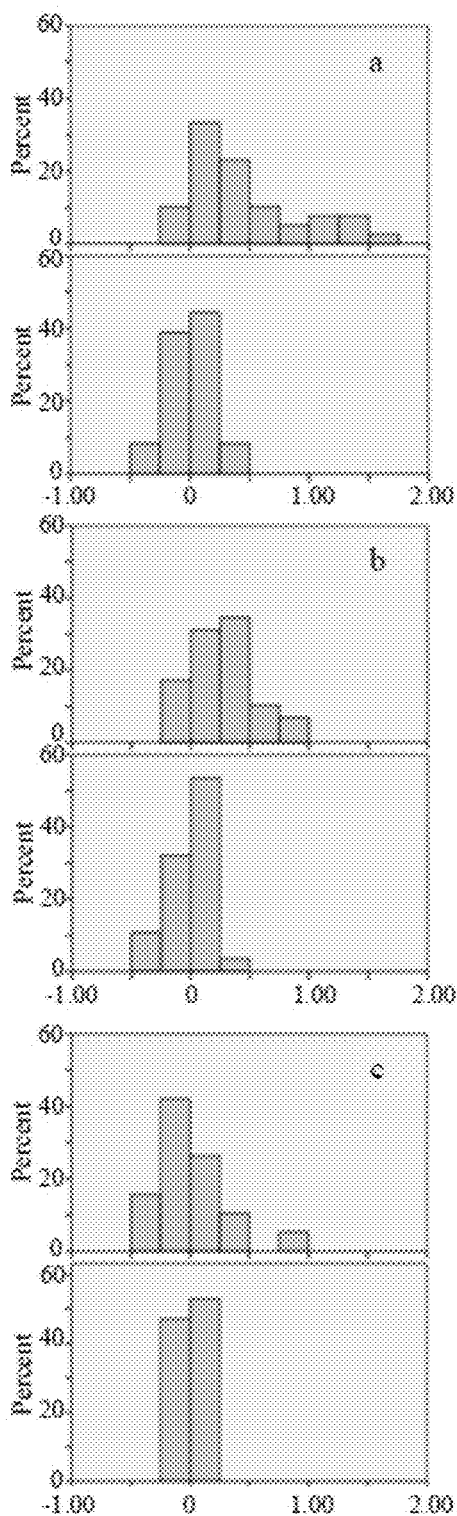

FIG. 16 is a schematic diagram showing cell treatment of nanoneedles according to another embodiment of the present invention;

FIG. 17 are SEM images of a diamond nanocone array with scale bars of 1 um represented in FIG. 15;

FIGS. 18a-b, FIGS. 18c-d and FIGS. 18e and 18f are optical microscopy images of diamond nanocone treated cells, smooth silicon substrate cells and smooth silicon substrate untreated cells, respectively, with FIGS. 18a, 18c and 18e of 10× in magnification, and FIGS. 18b, 18d and 18f of 20× in magnification;

FIG. 19 is a chart showing viability of cells which were not treated (bar A), treated by a smooth substrate (bar B), and treated by a diamond nanoneedle array (bar C);

FIG. 20 are charts showing flow cytometry analysis of the fluorescence intensities of control and nanocone treated MC-3T3 cells, in which FIG. 20(a) is a fluorescence histogram of control sample and FIG. 20(b) is a fluorescence histogram of the sample treated with the nanocone array;

FIG. 21 are charts showing flow cytometry analysis of the fluorescence intensities of untreated and nanocone treated MC-3T3 cells, in which FIG. 21a) is a fluorescence histogram of untreated sample and FIG. 21b is a fluorescence histogram of the sample treated with the nanocone array;

FIG. 22 are graphs showing schematic Distributions of $A_T^*$ and $A_C^*$ of measurements made on (a) the $3^{rd}$ day, (b) the $7^{th}$ day, and (c) the $14^{th}$ day; and

DETAILED DESCRIPTION OF EMBODIMENTS OF THE INVENTION

In the preamble of the specification, it is discussed that various approaches have been proposed to deliver biomolecules or therapeutic molecules to cells for treatment purpose. For example, the use of cell penetrating peptides (CPPs), electroporation, viral vectors and nanoneedles has been suggested before.

The use of CPP is one of the approaches to deliver different molecules into cells because this approach can be carried out in a non-invasive way. CPPs are short peptides that facilitate cellular uptake of various molecules. The molecules to be delivered are associated with the peptides either through covalent bonds or non-covalent interactions. While this method has great potential in that the CPPs act as delivery vehicles, there are limitations associated therewith. For example, studies have shown that the method is not functional when applied in certain cell lines (e.g. Madine Darby canine kidney cells). Further, studies have shown that the method has limited in-vivo applicability.

Electroporation can be used to increase the permeability of cell plasma membrane by applying an external electrical field so that a dug can enter cells. However, this approach often causes cell death.

Viral vectors can be used to deliver genes into cells. During application, the genes in the virus that cause disease is removed and replaced with genes encoding the desired effect. However, there are serious limitations such as infecting healthy cells, causing harmful mutations to DNA or even cancer. Studies have shown that they can even lead to death of a patient in a clinical trial.

Individual nanoneedles may be used separately. Studies leading to the present invention have shown that nanoneedles with diameter less than 400±136 nm can pierce cell membranes without causing irreversible destruction of the membrane with insertion that lasts up to 1 hour. Nanoneedles have been demonstrated to deliver fluorescent quantum dots into the cytoplasm and nuclei of living cells, but, among other shortcomings, one shortcoming is that it is very time consuming if one needs to treat a large number of cells.

To increase the efficacy, arrays of bundles of nanotubes have been also employed. One nanotube however would not be strong enough, although a bundle of 5-10 nanotubes together can be sufficiently strong. The shortcomings of this technique include: (1) the tip diameter of each tube is usually one micrometer or above, (2) the bundled nanoneedles will have relatively uniform diameter for their whole length and it is very difficult to maintain strength for piercing large cell membranes to deliver drugs to cell nuclei when the required nanoneedle length is long (e.g., close to 100 um), (3) since the internal nanotube diameter is very small (below 200 nm or even 100 nm or even 70 nm), it is difficult to absorb a reasonable high amount of large drug molecules into the tube (for example, plasmid DNA length from 0.3 to 66 nm, chromosome DNA is much larger).

To address these limitations, the present invention has been developed to provide a novel technique using arrays of nanoneedles with specific physical parameters, mechanical properties and application requirements to deliver a substance to a subject. Since different factors play into the effectiveness and efficiency of substance delivery, only specific combinations of these factors can lead to successful delivery of the substance.

In one specific embodiment, the present invention is concerned with an apparatus having an assembly with a plurality of the nanoneedles for delivering the substance into the subject, each of the nanoneedles has non-uniform diameter with a wider upper end and a narrower lower end (at the opposite end) and a length from 5-100 um (although studies have shown that the length may range from 200 nm to 100 um). This length ensures that the needles are sufficiently long to reach within the interior of the cells. The upper end has a diameter from 1-20 um and the lower end has a diameter from 50-400 nm. Studies have shown that while the tip diameter may range from 20-436 nm or more preferably 50-400 nm (which is a workable range for most cell types) in that the needles with this tip dimension do not impair the cell viability, the tip diameter may be more preferably range from 50-100 nm. This is advantageous in that it can significantly speed up the delivery of the substance into the subject.

Figure 1:
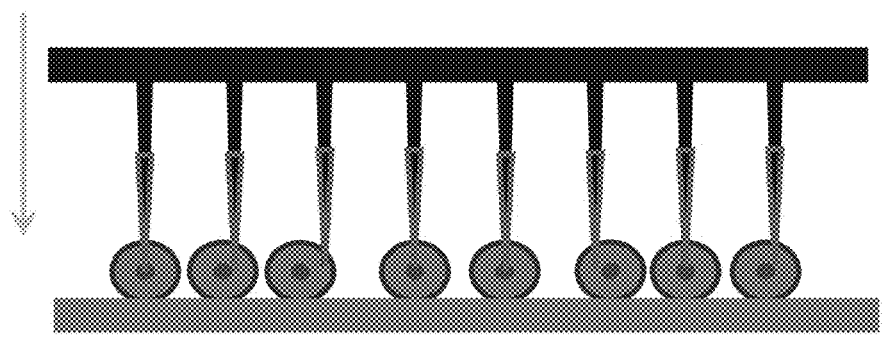
FIG. 1 is a schematic diagram showing delivery of a substance to within living cells by an apparatus according to an embodiment of the present invention.

The nanoneedles are configured such that they are non-hollow. In other words, a substance to be delivered by the needles does not pass through the needles. The non-hollow configuration means that when compared with tubes or pipes the rigidity of the needles is much improved. Even when the needles are constructed to be relatively thin yet sufficient rigidity thereof is still preserved. The nanoneedles are rigid enough such that they do not rely on bundling nanoneedles together in a penetration exercise. In use, the cells are collected on a substrate which may be a multi-well array of a container. Alternatively, the substrate may be a planar member for providing a surface on which the cells rest during the penetration. FIG. 1 shows the resting of the cells on the substrate surface.

The nanoneedles may be made from a material that allows them to maintain rigidity during a subject penetration process. The material which is to be used will be discussed further below.

FIG. 1 demonstrates that the nanoneedles are configured to adopt a generally conical profile. The lower end of the nanoneedles is pointy and sharp. This profile facilitates the piercing of cell membrane by the tip of the nanoneedles. In the embodiment shown in FIG. 1, the diameter of the tip of the needles ranges from 20-436 nm, the needles in this embodiment can still satisfactorily pierce through the cell membrane and deliver the substance without causing irreversible damage to the cell membrane. In this embodiment, the nanoneedles are spaced from each other and the spacing between adjacent nanoneedles is from 5-50 um depending on the types of cells. It can be seen from FIG. 1 that the plurality of nanoneedles together takes the form of a nanoneedle patch. The nanoneedle patch has a nanoneedle density of $10^5$-$10^6$ nanoneedles per $cm^2$. In order to deliver efficiency, a patch with at least 600 such nanoneedles is required. With this spacing and number of nanoneedles, the nanoneedles are densely packed enough to allow piercing of large number of cells for many cell types in one go. This can facilitate the speed of treating or delivering of a substance into the cells in an efficient manner.

The apparatus is provided with means such that the nanoneedle patch can be applied to the cells to be treated at a speed of 0-5 m/s, although a more preferable rate is 0-3 m/s. With this feature, treatment of a large number of cells can be performed efficiently in an automated manner.

Figure 2:
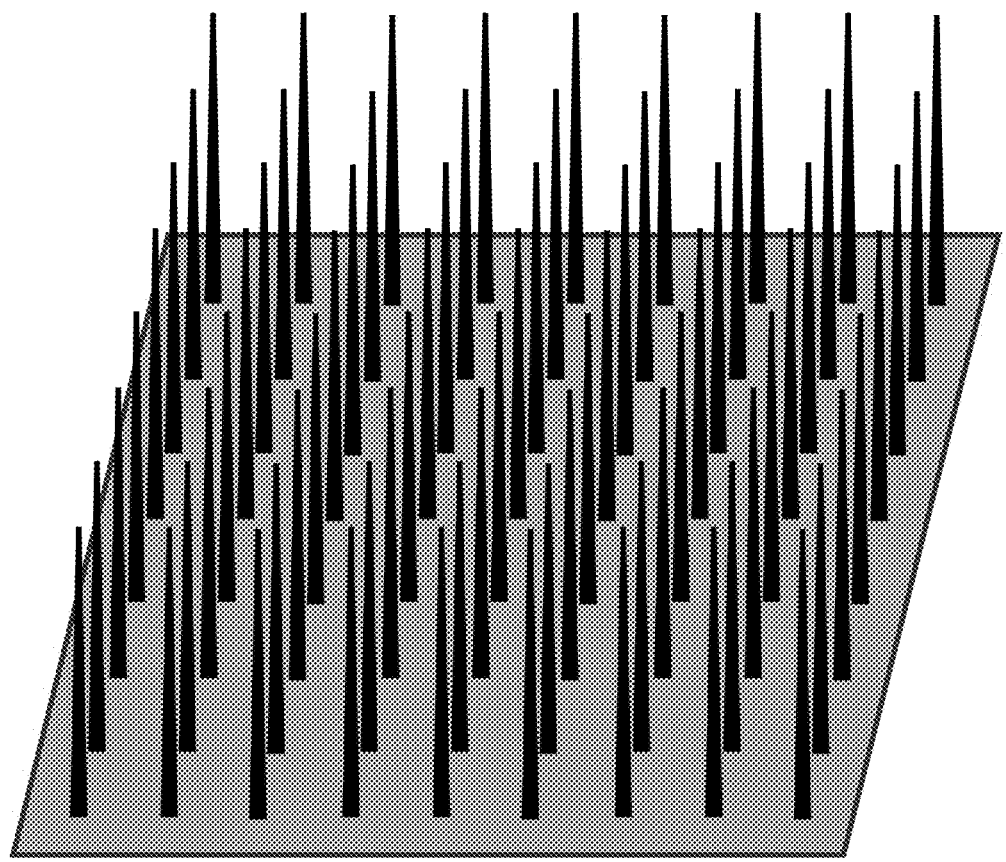
FIG. 2 is a schematic diagram of a nanoneedle patch for use in the apparatus of FIG. 1 according to an embodiment of the present invention.

FIG. 2 is a schematic diagram of a nanoneedle patch. The nanoneedles can be made of diamond. In one example, the diamond nanoneedle structures were grown from deposition of diamond and cBN films followed by a post-deposition reactive ion etching (RIE) treatment. The films were pre-coated through a gold etching mask and then etched in hydrogen/argon-based microwave plasma with the assistance of a negative substrate bias. Through this process, nanoneedle structures can be fabricated. The exact geometry, density and aspect ratio of these nanoneedle structures can be adjusted by controlling the etching mask design, microwave power, substrate temperature, and etching duration.

After fabricating the nanoneedle structures, the lower end, or tip, of the cones are to be treated such that they will carry a substance to be delivered into the cells. The substance may be attached to the tip in a number of different ways. In one embodiment, the substance, e.g. drugs or genes, may be coated onto the surface of the tip. In this particular embodiment, the substance is plasmid EGFP DNA and CdSe quantum dots (QDs). The plasmid EGFP DNA and CdSe QDs are dry-coated on the surface of nanoneedles for subsequent delivery. One approach of coating the DNA or QDs onto the nanoneedles is by use of a viscosity enhancer (e.g., methylcellulose, honey). Specifically, a coating solution is prepared. For example, the solution may contain either pEGFP DNA or CdSe QDs, methylcellulose as viscosity enhancer, and poloxamer (F-68) as surfactant. Then the DNA or QDs can be coated onto micro-nanoneedles using some coating methods.

Another approach of coating the DNA or QDs is by way of using disulfide bonding. With this approach, a thin layer of gold (~10 nm) is firstly deposited on the micro-nanoneedle structure. Then, a $NH_2$-terminated self-assembly monolayer is formed by the chemisorption of thiols on gold. The biotinylated DNA containing a disulfide bond can then conjugate to the surface. As far as QD coating is concerned, a third step will be conjugating sulfo-NHS—SS-biotin and introducing a further step to bind streptavidin-coated CdSe QDs by the specific binding of streptavidin and biotin. Streptavidin-coated CdSe QDs is a product that can be purchased on the market. Once the micro-nanoneedle is in water or inserted into an interior cellular environment, DNA will be released as most disulfide bonds are reduced into thiol groups (R—SS—R+2H++2e---->R—SH+SH—R).

It is to be noted that the above embodiment of a delivery apparatus does not require the use of a reservoir for supplying the substance to be delivered. The free of such reservoir allows a user to deliver of the substance to target cells more easily and efficiently because the user does not need to fill up a liquid substance to the reservoir. It is also to be noted that the needles are solid and this removes complications of engineering a very small channel within tube or pipe structures and delivering substances via such structures.

In an alternative embodiment, there is provided a system in which the nanoneedles are free of coating of a substance to be delivered into a subject. In such embodiment, the apparatus comprises a nanoneedle patch for introducing holes to the membrane of the cells of the subject suspended or immersed in a substance-containing fluid. During penetration of the cell membrane, the substance-containing fluid can enter and diffuse into the cells via the holes.

Yet in a different embodiment, there is provided a system in which the nanoneedles when manufactured are not coated with a substance to be delivered into a subject. The substance is provided to the tip of the nanoneedles just before they are to penetrate the cells. The may be achieved by first dipping a nanoneedle patch into a solution containing the substance to be delivered to the subject (e.g. a drug). The dipping of the patch allows the drug to absorb to the surface of the tips and/or in between the tips. Then, the patch can be used to pierce the cells to deliver the drug to the interior of the cells.

Further Embodiments of the Present Invention, Experiments and Experimental Results Therefrom Centrifugation Approach In this embodiment, a novel platform utilizing centrifugation-induced supergravity is used to precisely control a diamond nanoneedle array to facilitate cytosolic delivery into living cells. By using such platform, the cellular membrane is penetrated and disrupted by the nanoneedles to reliably achieve diffusion based cytosolic deliveries. Experimental data demonstrated (as illustrated below) that this technique is applicable to different types of cells, including primary neuron, for delivery of various molecules and materials in a high throughput manner. Introducing molecules into neurons had been notoriously difficult in the past.

Results

Delivery Approach and its Working Principle

Figure 3:
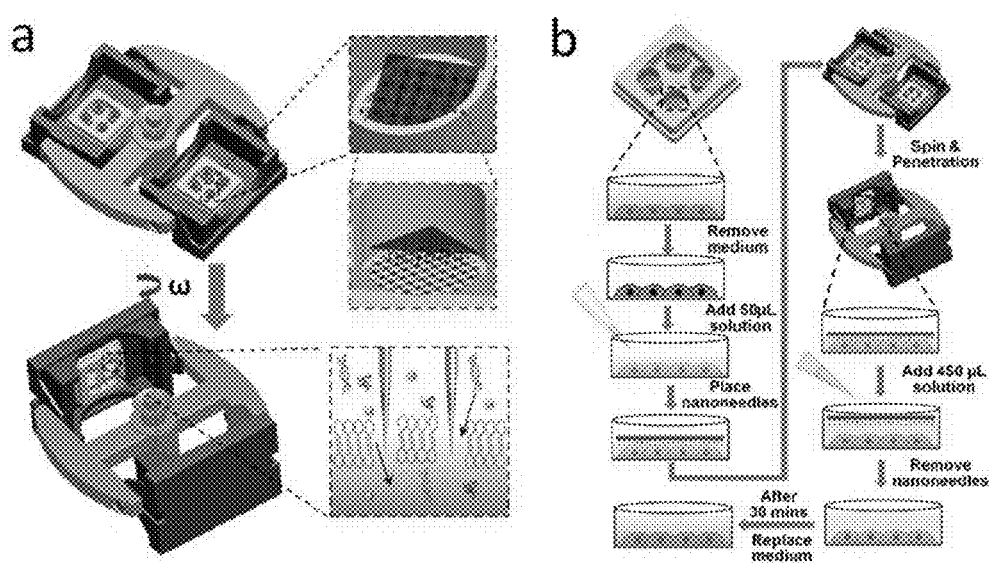

The principle of the nanoneedle array based delivery system is illustrated in FIG. 3. When a nanoneedle array is applied to the cells with controlled force, the nanoneedles can penetrate into and disrupt the cell membranes. The penetration and subsequent disruption of cell membrane by nanoneedles was precisely-controlled by centrifugation-induced supergravity to achieve reliable, highly efficient, diffusion based cytosolic delivery. Depending on the exact size of the nanoneedles and the control of the penetration process, the induced temporary disruption, or holes, in the cell membrane can be accessible to materials from the surrounding medium, which can directly diffuse into cell cytoplasm before the recovery of the disruption. To implement this approach, especially for but not limited to adherent cultured cells, the nanoneedle array was gently placed on top of cells with the needles facing toward cells. In order to carefully control the force applied to poke the cells, the whole setup was maintained in a supergravity environment by centrifuging at optimized speeds. By changing the centrifuging speed, the interaction force between the nanoneedles and cell membranes can be controlled accordingly. Unlike previous methods using single nanoneedle to address individual cells with expensive equipment like AFM, the technique used in this this embodiment does not rely on any special equipment, while yet still provides sufficient control to achieve proper disruption of cell membranes for intracellular delivery purpose.

Fabrication of Diamond Nanoneedle Array

There had been proposals of fabricating fine needles for delivery of substance. However, these proposals were theoretical and were not either not realistic or not enabling in that the would-be needles could not be made. In order to perform high-throughput cell-penetration based cytosolic delivery, one embodiment of the present invention is concerned with fabrication of diamond nanoneedle arrays as shown in FIG. 4. FIG. 4$a$ is an overall view (scale bar, 10 um) and FIG. 4$b$ is a detailed view (scale bar, 2 um) of a nanoneedle array by SEM. Diamond was chosen for its superior mechanical strength and inertness, which among other advantages render the nanoneedle arrays durability and biocompatibility. Materials with sufficiently similar physical characteristics as diamond can also be used. In this embodiment, the individual nanoneedle was measured at 326±110 nm in tip diameter and 4.55±0.68 μm in length, with a density of substantially $6.6 \times 10^4/mm^2$. The optimal dimensions of the nanoneedles can vary for distinct type of cells.

Cytosolic Delivery

To demonstrate the effectiveness the delivery system of the present invention as described, a live/dead (calcein AM/ethidium homodimer-1) staining kit to characterize the delivery efficiency in fibroblast cells was firstly used. This kit has been widely used to characterize cell viability and cytotoxicity. In the assays, with application of nanoneedle array to cells, the membrane-permeant calcein AM enters cells and is cleaved by esterases in live cells to yield cytoplasmic green fluorescence; while the membrane-impermeant ethidium homodimer-1 (EthD-1) labels nucleic acids of membrane-disrupted cells with red fluorescence. The observation of both green and red fluorescence in treated cells indicates that successful cytosolic delivery of molecules (EthD-1) is achieved without significantly injuring them (FIG. 5). In comparison, dead cells were labeled with only red fluorescence (FIG. 5). FIG. 5$a$ are representative images of fibroblast cells after successful cytosolic delivery of EthD-1; FIG. 5$b$ is a chart showing quantification of delivery efficiency; and FIG. 5$c$ is a chart showing quantification of cell viability after being treated with nanoneedles arrays; all at a scale bar of 100 um.

In an embodiment, the penetration and subsequent disruption of cell membrane by nanoneedles was precisely controlled by centrifugation-induced supergravity to achieve reliable, highly efficient, diffusion based cytosolic delivery. In a specific embodiment, in order to optimize the force applied onto the cell membranes through nanoneedles, the whole setup (cell culture plus nanoneedle array) was maintained in supergravity by centrifugation at a series of speeds from 300 rpm (12.8 g, RCF) to 1000 rpm (142 g). As shown in FIG. 5$b$, when the centrifuging speed increased from 300 rpm to 500 rpm (35.5 g), the cytosolic delivery efficiency of EthD-1 improved significantly from ~5% at 300 rpm to ~80% when the speed was 500 rpm or above, without causing much increase in the number of damaged cells (FIG. 5$c$).

Application to Primary Neurons

Intracellular delivery into post-mitotic cells, such as neuron, has always been challenging. To demonstrate that a method according to the present invention as a promising universal alternative for cytosolic delivery applications, the method was tested on primary hippocampal neurons. Compared with fibroblast cells, neurons are more vulnerable to membrane disruption induced by nanoneedle arrays. Generally, a relatively lower speed would be required to achieve similar delivery efficiency as in fibroblast cells (FIG. 6). The optimal centrifuging speed was shown to be around 300 rpm (lowest among tested speeds, 12.8 g), at which about 80% delivery efficiency of EthD-1 was realized. Gradually raising the speed to 700 rpm significantly increased the cell death rate to more than 20%. Therefore, a centrifuging speed of 300-400 rpm was selected for following experiments with primary neurons. FIG. 6$a$ are representative images of fibroblast cells after successful cytosolic delivery of EthD-1; FIG. 6$b$ is a chart showing quantification of delivery efficiency; and FIG. 6$c$ is a chart showing quantification of cell viability after being treated with nanoneedles arrays; all at a scale bar of 100 um.

Universal Delivery Method for Various Materials

In addition to small molecule (e.g. EthD-1), further investigation was conducted to determine whether the method can facilitate the cytosolic delivery of a wide range of molecules and materials into primary neurons. As shown in FIG. 7$a$, fluorescently labeled antibody (Donkey IgG) can be successfully delivered to cytoplasm of neuronal cells using our technique. Intracellular delivery of nanoparticle of different sizes and properties were then demonstrated. The results show that quantum dots (QDs, 20 nm in diameter) were rapidly delivered into neurons in less than 30 min after nanoneedle treatment (FIG. 7$b$). The QDs were uniformly distributed across all cytoplasm area without any aggregation, which has been difficult for traditional methods (FIG. 7$b$'). Similar delivery dynamics was also achieved for large polystyrene nanoparticles (200 nm in diameter, FIG. 7c). A 3D-reconstruction of the Z-series scanning confirmed that the delivered nanoparticles were actually inside the cells (FIG. 7c'). In the control experiments, where the neuron cells were exposed to the nanomaterials (QDs & polystyrene particles) without being treated with the nanoneedles, only minimum fluorescent signal was observed (FIG. 7d), indicating that endocytosis was not mainly responsible for the nanoneedle-array-facilitated delivery.

FIG. 8a, FIG. 8b and FIG. 8c are bright field, fluorescent image, overlay image of neuron cells at one day after transfection by nanoneedle arrays, respectively. (Scale bar, 200 μm) FIG. 8d illustrates comparison of the transfection efficiency between nanoneedle based technique and traditional lipofection method at different incubation times.

The delivery of nucleic acids (NAs) into cells is crucial for the study of many aspects of neurobiology. Therefore, the ability of our system to facilitate the delivery of plasmid DNAs into neuronal cells was investigated. Protein expression from plasmid DNAs requires the transport of DNAs into cell nucleus. The commonly used lipofection technique usually gives poor results in post-mitotic cells in terms of transfection efficiency (1-5% in primary neuron). Also, the protocol is typically time-consuming (several hours) due to the endocytosis based internalization of DNA-lipid complexes. In the method, to protect DNA from degradation and help the transport from cytoplasm into nucleus, the plasmid DNA was still complexed with lipid molecules. The complexes were then delivered into cells with nanoneedles treatment followed by incubation for a short period of time (5-30 min). As shown in FIG. 8, a transfection rate of around ~45% in primary neuron was consistently achieved with our technique. Compared with traditional lipofection in primary neuron (FIG. 8), the nanoneedle array based technique significantly increased the transfection efficiency by 8 folds, with a dramatically shorter (10 minutes VS a few hours) experimental protocol without using any special equipment.

FIG. 9a is a stitched phase-contrast image of a neuron culture treated by a nanoneedle patch. FIG. 9b is a stitched fluorescent image of neurons transfected with GFP. In panel a) and b), red squares indicate the area covered by the nanoneedle patch, scale bar, 1.6 mm. FIG. 9c) is an enlarged view of the yellow line boxed regions in panel a). FIG. 9d) Enlarged view of the yellow line boxed regions in panel b). FIG. 9e) is a merged image of neuron cells combining phase-contrast and GFP channels, scale bar, 150 μm. FIG. 9f) is comparison of the transfection efficiency between nanoneedle based technique and traditional lipofection method at different incubation times, error bars indicate s.e.m from three independent experiments. *P<0.01, determined by ANOVA analysis.

FIGS. 10a) to c) are GFP fluorescence images showing successful delivery of DNA plasmid into neurons of 2-3DIV, 9-10DIV, and 12-13DIV, respectively. FIGS. 10a') to c') are merged images combining GFP and phase-contrast (or bright-field) images showing the status of neuron culture of different stages, scale bar, 200 μm.) FIG. 10d is a graph showing quantification of delivery efficiency in neurons of different stages using the nanoneedle based technique; error bars indicate s.e.m from three independent experiments.

Discussion

In this embodiment, it is demonstrated that centrifugation can enhance in intracellular delivery reliably and efficiently without using vectors. In this method, a diamond nanoneedle array was used to penetrate and temporarily disrupt the cell membrane in a well-controlled manner to facilitate reliable and highly efficient intracellular delivery. This technique is applicable to different type of cells, including primary neuron, which is post-mitotic and usually difficult to treat with traditional methods. The approach is also suitable for a wide range of molecules and materials, including small chemicals, antibodies, quantum dots, nanoparticles and nucleic acid etc. These results demonstrate the powerful capability of the system of the present invention as a universal alternative for intracellular delivery. Unlike many current methods such as cell penetrating peptide (CPP) or nanomaterials based techniques, this method is independent of molecular structure, size (below the size of nanoneedles) and surface chemistry, which renders significant freedom in designing novel sensors based on different molecules and materials, and greatly expands the ability to study intracellular processes with these novel probes.

Similar to electroporation and microinjection, the technique of this embodiment is based on a membrane disruption mechanism, so that exogenous materials in the medium can freely diffuse into cell cytosol through the access ports induced by the penetration of arrays of nanoneedles. The advantages over current electroporation or microinjection are obvious: no electrical field or any special device is needed in our technique, and the most sensitive cargo materials such as signaling proteins and QDs can be delivered intact without being affected by electrical field or chemicals. Meanwhile, it is demonstrated there is very high viability (~90%) in both fibroblast and neuronal cells after treated with the nanoneedle array, which is achieved by simple but reliable control of the penetration of nanoneedles into the cells with centrifugation-induced supergravity (FIG. 3). The force applied on cells through single nanoneedle is around 2 nN, when the centrifugation speed is around 300 rpm (12.8 g). Importantly, such precise control of the interaction between nanoneedles and cell membranes was achieved without using any special equipment, and guaranteed consistent disruption of cell membrane for reliable intracellular delivery. In contrast to previous studies where AFM with single nanoneedle tip was used to poke cells with very delicate manipulations, the system's ease-of-use and high throughput capability give the potential to be readily adopted in many research and clinical applications.

These results show that the endocytotic pathway is not heavily involved in the process of nanoneedle facilitated delivery of various molecules and materials, and indicated a diffusion dominated process. It appears that diffusion is mainly responsible for the intracellular delivery through membrane disrupted by mechanical restriction. However, before optimization, it is relatively difficult to directly disrupt the nucleus membrane for cargo molecules and materials to be delivered into the cell nucleus. In these cases, a second mechanism can be engaged to facilitate the transport from cytosol to nucleus. In the present study, specifically for plasmid DNA, the nanoneedle array based technique can be combined with lipofection, and this can significantly improve (about 8 folds) the lipid-medicated transfection efficiency in post-mitotic neurons. Even the cells were incubated with NA-lipid complexes for only 5 minutes, significant transfection of neurons (~20%) were still observed (FIG. 8d). Such reduction in required incubation time (for cells and DNA-lipid complexes) not only minimizes the cytotoxicity of lipid chemicals at high concentrations, but also dramatically increases the turnover and throughput of cellular assays involving gene manipulations. The design and fabrication of nanoneedle arrays can be further improved to facilitate direct delivery of materials into cell nucleus.

In summary, it is demonstrated that a novel platform utilizing a diamond nanoneedle array and making use of centrifugation can facilitate vector free, highly efficient and ultrafast cytosolic delivery. Using this system, the cellular membrane penetration and subsequent disruption by the nanoneedles was well-controlled by centrifugation-induced supergravity to achieve reliable, highly efficient, diffusion based cytosolic delivery. It is shown that this technique is applicable to different types of cells, including primary neuron, for universal delivery of a broad range of molecules and materials, including small chemicals, antibodies, QDs, nanoparticles and plasmid DNA, etc., in a high throughput manner. Also, the ease-of-use of this technique gives it the potential to be readily adopted in many research and clinical applications.

Methods and Materials

Nanoneedle Array Fabrication

The fabrication is based on two processes: deposition of nanodiamond film, and subsequent bias-assisted reactive ion etching (RIE) by electron cyclotron resonance (ECR) microwave plasma chemical vapor deposition (MPCVD). N-type (001) silicon wafers of 3 in. in diameter were used as substrate. Prior to nanodiamond deposition, the substrate was ultrasonically abraded for 60 min in a suspension of nanodiamond powders with a grain size of 5 nm in ethanol. Nanodiamond films of 7 μm thick were deposited in step one using a commercial ASTeX MPCVD equipped with a 1.5 kW microwave generator. The nanodiamond deposition was performed in the plasma induced in a 10% $CH_4/H_2$ mixture at a total pressure of 30 Torr and total gas flow rate of 200 sccm. The microwave power and deposition temperature were maintained at 1200 W and 800° C., respectively. After finishing the nanodiamond film deposition, the second step of RIE was performed using ECR MPCVD. The ASTeX microwave source employed a magnetic field of ~875 Gauss generated by an external magnetic coil. The RIE conditions were as follows: $H_2$ was used as the reactive gases at a total flow rate of 20 sccm; the substrate bias was −200 V; the reactant pressure $7 \times 10^{-3}$ Torr. The etching duration was 3 hour; and the input microwave power 800 W, respectively. The morphology of diamond nanoneedle patch was characterized by a Philips FEG SEM XL30. The sample was tilted 90° C. for scanning electron microscopy.

Cell Cultures

NIH3T3 fibroblast cells were maintained in dulbecco's modified eagle medium (DMEM, Life Technology) supplemented with 10% fetal bovine serum (FBS, HyClone), L-glutamine and penicillin/streptomycin. Cells were used for delivery experiments at around 80% confluency.

Hippocampal neuron cultures were prepared following the method previously described. Briefly, dissociated neurons were prepared from hippocampi dissected from E18 Sprague Dawley rats by enzymatic treatment with papain (Sigma) for 30 min at 37° C. followed by trituration with a 1 ml pipette tip. Before seeding neurons, all substrates were pre-coated with polylysine (Sigma, 100 μg $ml^{-1}$) and laminin (Invitrogen, 10 μg $ml^{-1}$). Neuron cells were treated with nanoneedle arrays at 6-7 days in vitro (DIV).

Delivery Procedure

Nanoneedle array was placed to float on culture medium with the needles facing toward cells. The medium containing various materials (fluorescent dye, antibody, nanoparticle, DNA, etc.) was then gradually removed to leave only a thin layer of solution between the needles and cell membrane. The whole setup was centrifuged at various speeds for 1 minute. After centrifugation, the medium was immediately put back to the culture well and lift off the nanoneedle array. After 5-30 minutes, fresh medium was used to wash off extra cargo materials. Chips with nanoneedle array were cleaned with piranha solution for one hour before reuse.

For intracellular delivery of small molecules (EthD-1, Life Technology), antibodies (Alexa 647 labeled Donkey IgG, Life Technology), QDs (625 nm emission wavelength, Wuhan Jiayuan) and polystyrene beads (200 nm, Wuhan Jiayuan), cells were incubated with these materials for 30 minutes before examination of delivery status by florescent imaging. To deliver GFP plasmid DNAs, the DNAs were firstly complexed with lipofectamine (Life Technology) for 10-15 minutes, and applied to treated cells for 5-30 minutes. Cells were then cultured overnight before imaging of GFP expression.

Image Acquisition

Samples were imaged on an Olympus IX81 microscope equipped with a motorized stage, cooled sCMOS camera and a 10× objective (0.4 NA) and a 20× objective (0.7 NA). Images were taken using Micromanager, and analyzed with Image J.

Apply Cell Suspension to Diamond Nanoneedle Array for High-Throughput Intracellular Delivery FIG. 11 is a scanning electron microscopy (SEM) image of an array of fabricated nanoneedles made of entirely of diamond according to an embodiment of the present invention. Distal tip (e.g. cell penetration) has a width of 135±20 nm (mean±standard deviation). Region adjacent the distal tip, pillar top end, has a diameter of 528±206 nm. Base region of the nanoneedles extending from a sporting structure has a diameter of 1.60±0.31 μm. The length of the nanoneeldes is substantially 7.42±1.35 μm. The density nanoneedles extending from the supporting structure is substantially $1.1 \times 10^6$ nanoneedles per $cm^2$. This density refers to the ascertained density over an area with 600 nanoneedles in 7 representative SEM images. In this embodiment, despite manufacturing challenges diamond was chosen as the material together with other features such as the dimensional features, because of its many superior properties. Diamond is the hardest material in nature and has very high mechanical toughness. This ensures the mechanical strength of nanoneedles even when the diameter is at nanometer level. Moreover, it has extreme chemical inertness and excellent biocompatibility, which allows the nanoneedles to be safely used in biological and medical applications.

Studies leading to the present invention were conducted to demonstrate that an array of nanoneedles made of diamond can improve molecules in entering cells. Lumienscent iridium(III) polypyridine complex [Ir(ppy)$_2$(bpy-Et)](PF$_6$) (Hppy=2-phenylypridine; bpy-Et=4-(N-ethylaminocarbonyl)-4'-methyl-2,2'-bipyridine) was chosen in experiments to demonstrate the improved delivery of substance into cells. The complex was chosen because of its negligible nuclear uptake. Since this complex does not enter cell nuclei by diffusion, the experiments were conducted ti demonstrate deliverty of substance into cytoplasm and nucleus of cells.

In this embodiment, suspension with the subjects was applied to the nanoneedle array at a speed of about 3.0 m/s. After treatment with the nanooneedles, the cells were grown on a sterile glass coverslip for 19 hours followed by PBS washing and then investigated by fluorescence confocal microscopy. Negligible cell death was found under microscopy in the experiments. FIG. 12a is a representative image showing the intracellular delivery of the iridium(III) polypyridine complex to A549 cells. FIG. 12a demosntrtes that the complex introdced into the cells with the nanoneedles mainly localized in the perinuclear region which is evidenced by the formation of sharp luminescent rings surrounding the nuclei shown in the image. In comparison, FIG. 12b is the image of the control group in which the cells were incubated with the complex for 19 hours but not treated with nanoneedles before incubation. FIGS. 12a and 12b were taken under the same microscope settings. In this group, even though the cells had the capacity of uptaking the complex after 19-hour incubation, the fluorescence signal was extremely weak. These results clearly indicated that, with the nanoneedle treatment, a much higher quantity of the complex can be delivered into the cytoplasm of the cells. (The arrows in the figures indicate the cells in which direct nucleic delivery of the luminescent complex is achieved with diamond needles treatment. The scale bars in FIGS. 12a), b), e) and f) indicate 25 µm).

To further demonstrate that cells treated with the nanoneedles can have the molecules delivered to the cell nucleus, emission profiles of selected cells were measured. The fluorescence intensities in the cytoplasm of the two selected cells were normalized to be the same value and the fluorescence intensities in the nucleus of the two cells were compared. The representative results are shown in FIG. 12c for a nanoneedle-treated cell and FIG. 12d for a cell without treatment. It is evident that the fluorescence intensity in the nucleus of the nanoneedle treated cell is significantly stronger than that in the nucleus of the cell without the nanoneedle treatment (FIG. 13). The comparison reveals that nanoneedle treatment using the needles with the aforedescribed features is able to facilitate nucleus delivery. For the nanoneedle treated group, unexpectedly, a number of cells in which the fluorescence signal was almost evenly distributed in the entire cells were found. For this reason, it was not apparent to locate their nuclei (indicated by the arrows in FIGS. 12e and 12f).

The diamond nanoneedles used in these experiments were substantially 7.42 µm long. This is much longer than conventional nanotubes used in reported cases. Many reported conventional nanotubes in the past had been only 1-2 µm in length. The present invention is technically advantageous in that it can deliver molecules into not only cells but also nucleus of the cells.

Further experiments were conducted to demonstrate that nanoneedles made of diamond as described above can not only effectively facilitate intracellular and even nucleus delivery of fluorescent molecules without inducing significant cell death, but also able to deliver more complex molecules such as biofunctional drug, e.g. anticancer drug molecules. Specifically, studied were carried out to demonstrate that cisplatin as an anticancer drug can also be effectively delivered into A549 cells using the aforedescribed nanoneedles. Cisplatin is one of the most effective broad-spectrum anticancer drugs and has been extensively used in the clinic. Its working mechanism is to enter cancer cells and cause cross-linking of DNA, which ultimately leads to apoptosis of the cancerous cells. Increasing the cellular uptake efficiency of cisplatin will result in an elevated cytotoxicity of the drug. Before investigating the anticancer drug delivery function of the nanoneedles, possible cell death upon nanoneedle treatment alone was first ascertained. In the experiment, A549 cell suspension was flushed to the surface of a nanoneedle patch in the same way as that used for the delivery of the luminescent iridium(III) complex. The control group was the cell suspension without being applied to the nanoneedles. For both the nanoneedle treated and untreated groups, the cell suspension was aliquoted and plated into microplate wells (4 wells per group). 8 hrs (nanoneedle untreated group 1: UT1; nanoneedle treated group 1, T1) after cell plating, the medium in the corresponding groups was removed and fresh medium was added. The cell viabilities were measured at 72 hrs post plating for both groups. The result is shown in FIG. 14. The cells were treated with diamond nanotubes, cisplatin, or none, or both. UT (left bar) abd T (right bar) indicate that the cells were untreated or treated with nanoneedles, respectively. UT1 shows that the treated cells by neither nanoneedles nor cisplatin; T1 shows that the cells were treated with nanoneedles but not cisplatin; UT2 shows the cells were treated by cisplatin but not nanoneedles; and T2 shows the cells were treated by both nanoneedles abd cisplatin. The number of the cells in the groups without nanoneedle treatment was normalized to 100% (UT1). The mean value of the cell viability of nanoneedle treated cells (T1) is 92.0±6.9%. The p-value (unpaired t test) between the two groups is 0.17. This means that the viability of cells after nanoneedle treatment has no statistical difference with that of control group (not treated by nanoneedles). The result evidently indicates that diamond nanoneedle treatment of cells has negligible negative effect on the viability of A549 cells under our experimental conditions. This is significant improvement over commonly used electroporation technology.

To further demonstrate the function of the diamond nanoneedles in drug delivery, cisplatin (1 µM) in cell suspension was added and viabilities of the cells with and without nanoneedle treatment were measured. In the experiments, half of the cell suspension was not applied to the diamond nanoneedles (nanoneedle untreated control group UT2). The other half of the cell suspension was applied to the diamond nanoneedles (T2) in the same way as used in the luminescent complex intracellular delivery so that pores may be created to help cisplatin to diffuse into the cells. Subsequently, for both nanoneedle untreated and treated groups, the cell suspensions were aliquoted and plated into microplate wells (4 wells per group). At 8 hrs after cell plating, the medium containing cisplatin was removed and fresh medium without cisplatin was added. At 72 hrs post cell plating, the cell viability of each group was measured and the result is shown in FIG. 14. With 8 hrs cisplatin treatment, for the group in which cells were not applied to the diamond nanoneedles (UT2), the cell viability was 90.5±6.0%. If we compare the value of cell viability with that of control group (UT1), in which cisplatin was not added and cells were not applied to nanoneedles, the p-value is 0.1. This demonstrates that the cell viability was almost not affected by 8 hrs cisplatin treatment. In contrast, for the group being applied to the nanoneedle array and cisplatin (T2), the cell viability dramatically drops to 39.9±6.5%. This is a remarkable and unexpected improvement of the drug delivery efficacy. This also demonstrates that the diamond nanoneedles breach cell membranes effectively to allow a higher amount of drugs to enter cells causing cell death. The results shown in FIG. 14 are in line with the qualitative study shown in FIG. 15.

It is to be noted that in the experiment, 1 mL of cell suspension was treated using a nanoneedle array within around half a minute. One milliliter of cell suspension contained around 60,000 cells. It means that about 60,000 cells can be treated within only half a minute, through which intracellular delivery of the iridium(III) polypyridine complex and cisplatin was greatly facilitated. This efficiency is significantly higher than that could be achievable using conventional micro/nanoinjection.

Fabrication of Diamond Nanoneedles

In this embodiment, fabrication of the needles contains two main processes, namely, (1) deposition of nanodiamond film, and (2) subsequent bias-assisted reactive ion etching (RIE) by electron cyclotron resonance (ECR) microwave plasma chemical vapor deposition (MPCVD). Nanodiamond films were firstly deposited on an n-type (001) silicon wafer using a commercial ASTeX MPCVD equipped with a 1.5 kW microwave generator. The nanodiamond deposition was performed in the plasma induced in a 10% $CH_4/H_2$ mixture at a total pressure of 30 Torr and total gas flow rate of 200 sccm. The microwave power and deposition temperature were maintained at 1200 W and 800° C., respectively. An around 8 µm-thick nanodiamond film was grown for 20 hours. After finishing the nanodiamond film deposition, the second step of RIE was performed using ECR MPCVD. The ASTeX microwave source employed a magnetic field of ~875 Gauss generated by an external magnetic coil. The RIE conditions were as follows: a mixture of 45% Ar and 55% $H_2$ was used as the reactive gases at a total flow rate of 20 s/cm; the substrate bias was −200 V; the reactant pressure about $6 \times 10^{-3}$ Torr. The etching duration was 7 hours and the input microwave power 800 W. It was observed that Mo particles sputtered from the substrate holder was deposited onto the diamond surface and acted as etching masks during etching (denoted as a self-mask process), and the Mo particles were detached as diamond tips were formed. The morphology of diamond nanoneedle patch was characterized by a Philips FEG SEM XL30. No Mo was detected at diamond tips by energy dispersive spectroscopy (EDS).

Application of Cells to Diamond Needles

A549 cells were maintained as exponentially growing cultures in a Dulbecco's modified Eagle's medium (DMEM) with 10% FBS and 1% penicillin/streptomycin at 37° C. The cells were trypsinized and suspended in DMEM medium. There are about $6 \times 10^4$ cells in one milliliter. Iridium(III) polypyridine complex was added to the cell medium at a concentration of 0.1 µM. Subsequently, one mL of cell suspension was taken by 1 mL pipette and rapidly flushed onto nanoneedles. Then the suspension was collected by a pipette and rapidly flushed onto the nanoneedles again. The application was repeated for 10 times. Control experiment with applying cells to a smooth Si wafer was also investigated for intracellular delivery of fluorescent dyes (luminescent iridium (III) polypyridine complex and fluorescein) and negligible effect was observed on improving intracellular delivery (data now shown). Therefore, in this work, we used untreated cells as negative controls.

Live-Cell Confocal Imaging

A549 cell suspension in medium/DMSO (99:1, v/v) containing $[Ir(ppy)_2(bpy-Et)](PF_6)$ (0.1 µM) was prepared. Half of the cell suspension was used as a control while the other half was applied to the nanoneedles. Subsequently, the cells were grown on a sterile glass coverslip in a 35-mm tissue culture dish for 19 h. Then after washing with PBS, the coverslip was mounted onto slides for measurements. Imaging was performed using a confocal microscope (Leica TCS SPE) with an excitation wavelength at 405 nm. The emission was measured using a long-pass filter at 532 nm.

Cell Viability Measurement

Cultured A549 cells were trypsinized and suspended at a concentration of $6 \times 10^4$ cells/mL in DMEM medium with or without 1 µM of cisplatin. One mL of cell suspension was taken by 1 mL pipette and rapidly flushed onto nanoneedles for 10 times. Subsequently, cells were plated into 96-well microtiter plates. The cells were allowed to attach and grow for 8 h before medium was changed. Each condition was tested in quadruplicate. At 72 h after cell plating, cell viability was determined by a methyl thiazolyl tetrazolium (MTT) assay.

Apply Cell Suspension Containing Differentiation Medium to Diamond Nanocone for Improved Differentiation Another embodiment of the present invention is concerned with applying cell suspension containing differentiation medium to diamond nanocones for use of intercellular delivery, for example, in improving osteoblastic differentiation. The nanoneedles, or nanocones, since the nanoneedles are configured to assume a conical profile, are formed into an array to transport molecules to the cytoplasm of a great number of cells in one step efficiently. The nanocone array was fabricated by depositing a thin layer of diamond film on a silicon substrate followed by bias-assisted reactive ion etching. In this embodiment, the height of the diamond nanocones ranges from 200 nm to 1 µm with tip radii of substantially 10 nm (diameter 20 nm). Experiments by way of fluorescein and propidium iodide staining clearly demonstrated that there is dramatically enhanced delivery of fluorescein into cells without leading to noticeable cell death with the aid of such nanocone treatment. In order to demonstrate the effectiveness of such nanocones, experiments were performed in which MC-3T3 cells in differentiation medium were applied to the nanocone array for enhanced intracellular delivery of the medium. This was confirmed by the fact that nanocone treated cells experienced much higher differentiation ability at early stage in comparison with untreated cells. Overall, the results indicate that the diamond nanocone array provides a very simple but yet very robust approach to achieve delivery of molecules to a large number of cells effectively and efficiently.

Experiment

Nanocone Patch Fabrication

The diamond nanocone array was fabricated in an ASTeX® microwave plasma CVD reactor equipped with a 1.5-kW microwave generator. Pyramidal-shaped [001]-textured diamond films were firstly deposited on a (001) silicon wafer using bias-enhanced nucleation and maintaining the alpha growth parameters close to 3. Subsequently, an in-situ bias-assisted reactive ion etching process was applied. During the process, hydrogen was transferred into the microwave reactor at a gas flow rate of 200 sccm to maintain the reactant pressure at 40 Torr. The input microwave power and substrate temperature were 1500 W and 850° C., respectively. A negative substrate bias of −400 V was applied to the substrates throughout the etching process, inducing a bias current of 140 mA. The etching process was lasted 40 min to form the diamond nanocone array. The diamond nanocone array was sterilized by 70% ethanol for at least 30 min before the start of the experiments. The array was then washed with PBS (phosphate-buffered saline) for three times to remove all ethanol.

Cell Culture

Mouse MC3T3-E1 pre-osteoblasts, which can differentiate into osteoblasts, were used in the present study. The cells were cultured at 37° C. with 5% carbon dioxide ($CO_2$) and 95% humidified air in Dulbecco's Modified Eagle Medium (DMEM) (Gibco) supplemented with 10% fetal bovine serum (FBS) (Gibco). The medium was renewed every 2-3 days and confluent cells were subcultured through trypsinization.

Intracellular Delivery

Before intracellular delivery study, the potential effect of nanocone treatment on the viability and morphology of MC-3T3 cells were investigated and demonstrated by a methyl thiazolyl tetrazolium (MTT) assay and optical microscopy, respectively. Three groups of cells were studied. One group was untreated cells. Other two groups included the cells which were treated by smooth silicon substrate and diamond nanocone array. For treatment, a volume of 1 m MC-3T3 cell suspension was applied to the substrate with a speed of about 3 ms$^{-1}$ by a pipette (FIG. 16). After the application, the cell suspension was collected and pipetted to the substrate again with a similar speed. Such cell treatment procedure was repeated for 15 times. The same procedures were used in all experiments for enhanced intracellular delivery. Following cell treatment, cells were plated into 96-well microtiter plates. After 22 hours, morphology of each group of cells was observed by optical microscopy. After 24 hours, cell viability was determined by MTT assay.

Subsequently, the enhanced intracellular delivery capability of the diamond nanocone array was firstly assessed by investigating the fluorescence intensity of fluorescein sodium salt stain in treated cells by quantitative analysis through flow cytometry. MC-3T3 cells were harvested at a density of $10^4$ cells/ml. Fluorescien was added to cell growth medium at a concentration of 1 mg/ml. After the addition of fluorescein, a volume of 1 ml of this cell suspension was treated with the same method as that described above. Two experiments were arranged in investigating the intracellular delivery of fluorescein sodium salt. In one experiment, the negative control was to apply cells to a smooth silicon substrate without the nanocone array. In the other experiment, untreated cells were used as the control (i.e. neither nanocone array nor smooth Si substrate was used). After 15 min of staining, the suspensions of control and treated group cells were pelleted by centrifugation (Spectrafuge™ 16 M, Labnet) at 6000 rpm for 3 min, after which the supernatants were removed. The cell pellets were washed by 1 mL of phosphate buffered saline (PBS) and then resuspended throughly. The cell suspensions were centrifuged again at 6000 rpm for 3 min, and the cell pelletes were washed by PBS for 3 times in total. Finally, the cell suspensions were prepared with a concentration of $10^4$ cells in PBS and then immediately analysed using a flow cytometer (Becton DICKINSON, FACSCalibur cytometer) by counting $1 \times 10^4$ cells per sample. For blank analysis during flow cytometry, a cell suspension with a concentration of $10^4$ cells without fluorescein staining was also prepared. The diamond nanocone array was further tested for the promted delivery of differentitation agent to osteoblast cells. MC-3T3 cells were harvested at a density of $2.5 \times 10^4$ cells/ml. Cell differentiation was induced by adding 50 µg/ml ascorbic acid (Sigma, USA) and 20 mM β-glycerol phosphate (Sigma, USA) to the growth medium (named as "differentiation medium"). A volume of 1 ml of this cell suspension, containg $2.5 \times 10^4$ MC-3T3 cells, was treated by nanocone array patch in the same way as that used in fluorescein delivery. The treated cells were then transferred to 24-well plates. A total of 5 or 8 wells were filled with the treated cells in 1 ml of differentiation medium (i.e., N=5 or 8, respectively) (see FIG. 16). At the same time, the same number of wells with untreated cells with the same cell concentration were prepared and used as controls. The differentiaiton medium was replaced every 2 to 3 days and measurements were made on the $3^{rd}$, $7^{th}$ and $14^{th}$ days.

Cell Differentiation

At designated time points, i.e. on the 3rd, 7th and $14^{th}$ days, the cells were lysed using 100 µl of lysis buffer (0.1% Triton X-100 in PBS) for 10 min at 4° C. with gentle rocking. The lysate in each well was then separately transferred to different ependorffs. To separate the cell protein and debris, the lysate was centrifuged at 4° C. with a speed of 300 rpm for 10 min. The Alkaline Phosphatase (ALP) activity and protein level of the supernatant were then determined.

Total Protein Level: The cell protein content was measured by using protein dye (Bio-Rad) which was warmed to 37° C. before use. A volume of 10 µl of cell lysate for each sample was transferred to a 96-well plate, and then 200 µl of protein dye was added to each well. Furthermore, 10 µl of bovine serum albumin (BSA) at 6 different concentrations (0.50, 0.25, 0.125, 0.0625, 0.03125 and 0 mg/ml) were used to obtain a standard curve. The optical densities at 595 nm were measured with UV-Vis-IR Microplate Reader (Powerwave XS MQX200R). An average cellular protein level for each cell sample was recorded.

Alkaline Phosphatase (ALP) Activity: The alkaline phosphatase (ALP) activity, one of the typical markers for osteoblastic differentiation, was studied with alkaline phosphatase activity assay kit (Stanbio Alkaline Phosphatase Liqui-Color®). Alkaline phosphatase buffer and alkaline phosphatase substrate were mixed in a ratio of 5:1 and was warmed to 37° C. A volume of 10 µl of the supernatant from each ependorff prepared above was transferred to a 96-well plate. The 96-well plate with all supernatant to be measured was pre-warmed to 37° C. before adding 200 µl of ALP indicator into each well. The absorbance at 405 nm was measured by UV-Vis-IR Microplate Reader (Powerwave XS MQX200R) immediately in dark and was consecutively recorded every 1 min for a total of 4 min at 37° C. The enzymatic activity was normalized to the total protein concentration. An average normalized ALP level was then obtained for each cell sample.

Data Analysis: The experiments were repeated 3 to 5 times for measurements on different days. For each set of experiment, the ALP levels $A_C$ and $A_T$ for the control group and the treated group were measured. Since the normalized ALP levels on the control samples could vary for different sets of experiments, in order to combine all the data, we first transformed the data to $A_C^* = [A_C - <A_C>]/<A_C>$, where $<A_C>$ was the average ALP level for a control group in a particular set of experiments, and similarly the normalized net ALP levels in the treated samples as $A_T^* = [A_T - <A_C>]/<A_C>$. The distributions of $A_C^*$ and $A_T^*$ were compared using the two-sample Kolmogorov-Smirnov test (2-tailed).

Furthermore, the mean values of $A_T^*$ and $A_C^*$ were compared through the non-parametric Mann-Whitney U test (2-tailed). Cases with p<0.05 were considered as statistically significant.

Results

Diamond Nanocones:

FIG. 17 shows the SEM images of diamond nanocone array. The nanocones were highly densely packed. The heights varied from 200 nm to 1 µm. The tip radius of the nanocones is mostly below 10 nm. The density of the nanocones is over $10^9/cm^2$.

Figure 18:
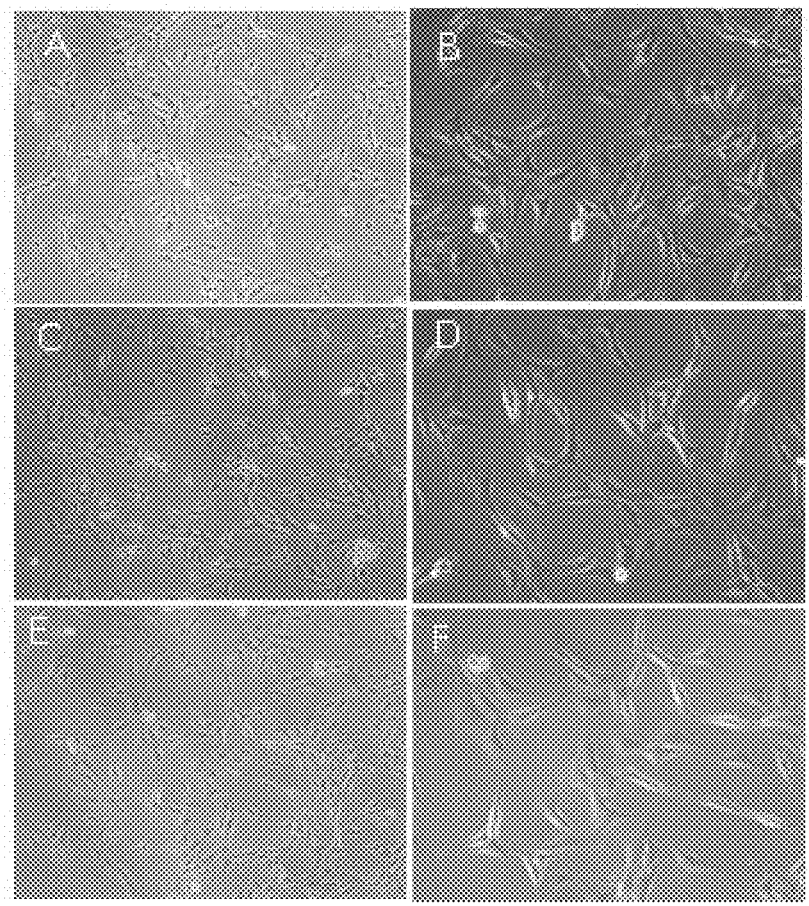

Effect of Treatment on Cell Morphology and Viability:

FIG. 18 represents the optical microscopy images of three groups of cells. FIGS. 18A and 18B show cells which were applied to diamond nanocone array and then plated to 96-well plate. FIGS. 18C and 18D are smooth silicon substrate treated cells while untreated cells are shown in FIGS. 18E and 18F. These images clearly reveal that cell morphology was not affected by either diamond nanocone or smooth silicon substrate treatment.

FIG. 19 displays the viability of cells with and without treatment. The same three groups (untreated cells, cells treated by either diamond nanocone or smooth silicon substrate) were investigated. The results indicate that both treatment methods, most importantly, diamond nanocone treatment did not cause noticeable cell death. The cell viability does not have statistical difference among groups (p>0.05). This is very important in using the technology for enhanced intracellular delivery.

Intracellular Delivery:

After confirming that both cell morphology and viability were not negatively affected by diamond nanocone treatment, the enhanced intracellular delivery was quantitatively assessed through flow cytometry. Two experiments were arranged with the same parameters (e.g. concentration of cells and fluorescein sodium salt) in investigating the intracellular delivery of fluorescein sodium salt. In one experiment, cells which were treated to a smooth Si substrate were used as a negative control, while in the other experiment untreated cells were used as a negative control. The results are shown in FIGS. 20 and 21. The cell population was divided into four groups according to their fluorescence intensities. The percentages of cells exhibiting fluorescence intensities of $1\times10^0$ to $1\times10^1$, $1\times10^1$ to $1\times10^2$, $1\times10^2$ to $1\times10^3$ and $1\times10^3$ to $1\times10^4$ were denoted as M1, M2, M3 and M4, respectively, in each histogram. FIG. 20 showed that the fluorescence dominated in M2 (viz., M2=63.1%) for the control sample, while the fluorescence dominated in M3 (viz., M3=73.5%) for the cells treated with the nanocone array. These results quantitatively and unambiguously showed that many more treated cells exhibited stronger fluorescence, which proved enhanced intracellular delivery by the nanocone array. On the other hand, FIG. 21 showed that the fluorescence dominated in M2 (viz., M2=70.0%) for the untreated sample, while the fluorescence dominated in M3 (viz., M3=62.4%) again for the cells treated with the nanocone array. The data of the nanocone treated cells in the two experiments are comparable, which demonstrated the repeatability of the method. When comparing the flow cytometry data of the cells which were treated by a smooth Si substrate and the untreated cells, it was found that treatment by the smooth silicon substrate did not enhance the intracellular delivery when compared to the untreated cells.

Furthermore, propidium iodide staining showed that the cells treated with the present diamond nanocones and the control cells demonstrated similar viability, which is a particularly desirable feature of the nanocones.

Alkaline Phosphatase Activity (ALP Activity):

The measurements made on the $3^{rd}$, $7^{th}$ and $14^{th}$ days, were repeated 5, 4 and 3 times, respectively. The data for $A_T^*$ and $A_C^*$ for measurements made on the $3^{rd}$ day denoted as $A_T^*(3)$ and $A_C^*(3)$, those for measurements made on the $7^{th}$ day denoted as $A_T^*(7)$ and $A_C^*(7)$, and those for measurements made on the $14^{th}$ day denoted as $A_T^*(14)$ and $A_C^*(14)$, are presented in Table 1 below together with the associated information, including the total number of measurements (N), their means and standard error (SE).

TABLE 1

Table 1. differentiation of cells. Data for $A_T^*(3)$, $A_C^*(3)$, $A_T^*(7)$, $A_C^*(7)$, $A_T^*(14)$ and $A_C^*(14)$, including the total number of measurements (N), their means and standard error (SE). The p values (2-tailed) between nanocone-array treated groups and controls for the two-sample Kolmogorov-Smirnov test, i.e., p (K-S test), and that for the Mann-Whitney U test, i.e., p (U test), are also shown.

|  | $A_T^*(3)$ | $A_C^*(3)$ | $A_T^*(7)$ | $A_C^*(7)$ | $A_T^*(14)$ | $A_C^*(14)$ |
|---|---|---|---|---|---|---|
| N | 39 | 36 | 29 | 28 | 19 | 17 |
| mean | 0.4681 | 0.0000 | 0.2541 | 0.0000 | 0.0124 | 0.0000 |
| SE | 0.0753 | 0.0300 | 0.0514 | 0.0312 | 0.0718 | 0.0298 |
| p (K-S test) | 0.000 | | 0.000 | | 0.594 | |
| p (U test) | 0.000 | | 0.001 | | 0.381 | |

FIGS. 22 (a) to (c) show the distribution of the results on $A_C^*$ and $A_T^*$, for measurements made on the $3^{rd}$, $7^{th}$ and $14^{th}$ days, respectively. Upper figures are for nanocone-array treated groups and lower figures are for the untreated control groups. For each set of experiment, the ALP levels $A_C$ and $A_T$ for the treated group and the control group were measured, and were then transformed to $A_T^*=[A_T-<A_C>]/<A_C>$ and $A_C^*=[A_C-<A_C>]/<A_C>$, where $<A_C>$ was the average ALP level for a control group in a particular set of experiments. The right shift of the distribution in nanocone-array treated groups indicates faster differentiation of cells. It is shown that the distributions for $A_C^*$ and $A_T^*$are very different for the $3^{rd}$ and $7^{th}$ days, while they are relatively similar for the $14^{th}$ day. In general, for the $3^{rd}$ and $7^{th}$ days, $A_T^*$peaks at a larger values and spreads over larger ranges when compared to $A_C^*$. The distributions of $A_T^*$and $A_C^*$ were compared through the two-sample Kolmogorov-Smirnov test (2-tailed). The p values are given in Table 1 as p (K-S test). The p values showed that the distributions of $A_T^*$and $A_C^*$ for measurements made on the $3^{rd}$ and $7^{th}$ days were significantly different, while those made on the $14^{th}$ day was not significantly different.

On the other hand, the mean values of $A_T^*$and $A_C^*$ were compared through the non-parametric Mann-Whitney U test (2-tailed). The p values are given in Table 1 as p (U test). The p values showed that the mean values of $A_T^*$and $A_C^*$ for measurements made on the $3^{rd}$ and $7^{th}$ days were significantly different, while those made on the $14^{th}$ day was not significantly different. From these results, we observed that the MC-3T3 cells having been pipetted down onto the nanocone array revealed significantly higher ALP activities on the $3^{rd}$ and $7^{th}$ days after treatment, when compared to the control samples, implying enhanced osteoblastic differentiation in the early period after treatment. On the other hand, we also observed that the treated cells did not show significantly higher ALP activities on the $14^{th}$ day after treatment, implying no enhanced osteoblastic differentiation in the later period after treatment.

Discussion:

In the present embodiment, we designed a highly densely packed nanocone array to mechanically disrupt cell membranes for enhanced delivery of drug molecules into a very high number of cells.

Diamond was selected to grow the nanocone array with such a small geometry because its significantly high Young's modulus ensured these ultra-small nanocones were mechanically robust enough to breach cell membranes. Moreover, its intrinsic biocompatibility might minimize harmful effects to cells.

The nanocones were highly densely packed with a density over $10^9/cm^2$ and sizes in nanometer range. They were designed to mechanically disrupt cell membranes to enhance intracellular delivery of drug molecules without causing irreversible damage. The geometry and the aspect ratios of these diamond nanocones were significantly different from those of the silicon nanowires employed by in the prior art such as Kim et al., which had diameters and lengths of about 90 nm and 6 μm, respectively.

In the present invention, cells were applied to the nanocones with a certain speed to temporarily rupture the cell membranes. The much shallower penetration of the nanocones into the cells would minimize the potential detriment to the cells through piercing all the way through the entire cells. To deliver drug molecules to a high population of cells without endocytosis, methods such as electroporation are most commonly used. Electroporation has been used to increase the permeability of cell plasma membrane by applying an external electrical field. However, this approach often leads to cell death. In contrast, the present intracellular delivery method has overcome such limitations. The enhanced drug delivery into the treated cells was verified by fluorescein staining through flow cytometry.

It should be understood that the above only describes the preferred embodiments according to the present invention, and that modifications and alterations may be made thereto without departing from the spirit of the invention. Further, a skilled person in the art will be familiar with the following prior art which is incorporated into the description herein in their entirety by way of reference.
1. Han S W, Nakamura C, et al. Biochem Bioph Res Co (2005) 332:633-639.
2. Yum K, Na S, et al. Nano Lett (2009) 9:2193-2198.
3. Zhang W J, Meng X M, et al. Appl Phys Lett (2003) 82
4. U.S. Pat. No. 6,261,554
8. EP1195440
9. U.S. Pat. No. 6,620,617
10. U.S. Pat. No. 7,112,442
11. WO2010/082008
12. S. Mehier-Humbert, R. H. Guy, *Adv. Drug Deliv. Rev.* 2005, 57, 733.
13. S. Han, C. Nakamura, I. Obataya, N. Nakamura, J. Miyake, *Biochem. Biophys. Res. Commun.* 2005, 332, 633.
14. K. Yum, N. Wang, M. Yu, *Nanoscale* 2010, 2, 363.
15. X. Chen, A. Kis, A. Zettl, C. R. Bertozzi, *Proc. Natl. Acad. Sci. U.S.A.* 2007, 104, 8218.
16. W. J. Zhang, Y. Wu, W. K. Wong, X. M. Meng, C. Y. Chan, I. Bello, Y. Lifshitz, S. T. Lee, *Appl. Phys. Lett.* 2003, 83, 3365.
17. W. Kim, J. K. Ng, M. E. Kunitake, B. R. Conklin and P. Yang, *J. Am. Chem. Soc.,* 2007, 129, 7228.
18. A. K. Shalek, J. T. Robinson, E. S. Karp, J. S. Lee, D.-R. Ahn, M.-H. Yoon, M. Jorgolli, R. S. Gertner, T. S. Gujral, G. MacBeath, E. G. Yang, A. Sutton and H. Park, *Proc. Natl. Acad. Sci.,* 2010, 107, 1870.

The invention claimed is:

1. A method of delivering substance to target cells, comprising steps of:
   a) providing a system comprising an assembly including a plurality of elongate non-hollow nanoneedles forming a nanoneedle array for delivering the substance into the cells, at least some of the nanoneedles having a non-uniform diameter with a wider upper end, a narrower lower end for penetration into the cells and a length from substantially 200 nm to 100 um, wherein the lower end has a diameter from substantially 20-436 nm, wherein adjacent nanoneedles are spaced apart by substantially 5-50 um for minimizing multiple nanoneedles penetrating into one cell causing cell death, and wherein:
   i) said nanoneedles are made from a material grown from pre-deposition and selected from the group consisting of diamond, cubic boron nitride, carbon nitride, boron nitride, boron carbon nitride, metal borides and essentially boron materials, followed by treatment of a post-deposition of reactive ion etching, thus forming a structure of said nanoneedles, allowing said nanoneedles to maintain sufficient thinness and yet adequate rigidity during penetration; and
   ii) 1) applying the nanoneedles onto the cells grown on substrates at a speed of 0<5 m/s;
       or
       2) applying the nanoneedles onto the cells grown on substrates with a centrifugation force from 0.5 to 10 nN;
       or
       3) applying the cells suspended in a fluid to the nanoneedle array at a rate from 1 to 10 m/s;
   b) allowing the substance be released or diffused from the nanoneedles into the cells intra-cellularly;
   c) applying the nanoneedle array to the cells under centrifugation at a speed from 300-1000 rpm (12.8-142 g); and
   d) allowing the substance to form a complex with a transfection reagent.

2. A method as claimed in claim 1, wherein the substance is or comprises genetic material.

3. A method as claimed in claim 2, wherein the genetic material is DNA or RNA.

4. A method as claimed in claim 3, wherein the transfection reagent is selected from a group including lipofactmaine, expifectamine, oligofectamine, cellfectin, and polyethylenimine (PEI).

* * * * *